(12) United States Patent
Gu et al.

(10) Patent No.: US 6,339,139 B1
(45) Date of Patent: Jan. 15, 2002

(54) RECEPTOR-MEDIATED GENE TRANSFER SYSTEM FOR TARGETING TUMOR GENE THERAPY

(75) Inventors: Jianren Gu; Peikun Tian, both of Shanghai (CN)

(73) Assignee: Shanghai Cancer Institute, Shanghai (CN)

( * ) Notice: Subject to any disclaimer, the term of this patent is extended or adjusted under 35 U.S.C. 154(b) by 0 days.

(21) Appl. No.: 09/092,000

(22) PCT Filed: Oct. 27, 1997

(86) PCT No.: PCT/CN97/00106

§ 371 Date: Aug. 26, 1998

§ 102(e) Date: Aug. 26, 1998

(87) PCT Pub. No.: WO98/18951

PCT Pub. Date: May 7, 1998

(30) Foreign Application Priority Data

Oct. 31, 1996 (CN) .......................................... 96 116557

(51) Int. Cl.[7] .......................... C07K 5/00; C12N 15/63
(52) U.S. Cl. ..................................... 530/300; 435/320.1
(58) Field of Search ..................... 435/6, 69.1, 91.31, 435/440, 455, 467, 325, 375, 320.1; 514/2, 44; 530/300, 303, 387.1; 536/23.1, 23.5, 24.31, 24.5

(56) References Cited

U.S. PATENT DOCUMENTS 5,547,932 A * 8/1996 Curiel et al. .................... 435/6
5,739,027 A * 4/1998 Kamb ...................... 435/240.2
5,843,659 A * 12/1998 Lehar et al. .................... 435/6

OTHER PUBLICATIONS

Mastrangelo, M.J. et al. Seminars in Oncology, vol. 23, No. 1, Feb. 1996, pp. 4–21.*
Mercola, D. et al. Cancer Gene Therapy, vol. 2, No. 1, 1995, pp. 47–59.*

* cited by examiner

Primary Examiner—Sean McGarry
Assistant Examiner—Mark L. Shibuya
(74) Attorney, Agent, or Firm—Nath & Associates PLLC; Harold L. Novick

(57) ABSTRACT

The invention relates to a gene transfer system binding to a growth factor receptor, comprising 4-element complex gene transfer system consisting of ligand oligopeptide/polycationic polypeptide/endosome release oligopeptide/exogenous DNA or 3-element complex consisting of ligand oligopeptide/polycationic polypeptide/exogenous DNA. The invention exemplifies E5, GE7, GV1 and GV2 systems and they can be targeted for the introduction of exogenous genes into malignant tumor cells or tumor vascular endotheliocytes. They are also able to highly inhibit the growth of tumor cells in animals while p15, p16 or $p21^{WAF-1}$ was used as exogenous genes. The system according to the invention is a new introduction system in tumor gene therapy.

43 Claims, 28 Drawing Sheets

RECEPTOR-MEDIATED GENE TRANSFER SYSTEM FOR TARGETING TUMOR GENE THERAPY

FIELD OF THE INVENTION

The present invention relates to a gene transfer system comprising a ligand oligopeptide for growth factor receptor, an endosome-releasing oligopeptide and a polycationic polypeptide to form a complex with exogenous gene either in the form of free DNA of a recombinant eukaryotic expression vector or in the form of a recombinant viral vector. Via receptor mediated endocytosis, exogenous DNA was targetably transduced into the tumor cells for the purpose of tumor gene therapy.

BACKGROUND INFORMATION

Gene therapy is to transduce the exogenous DNA into certain type(s) of human cells for the treatment of human diseases. For the therapeutic purpose, it is of prime importance to generate a gene transfer system with safety and high efficiency and targetability. So far as it is concerned, there are two types of systems currently used to transfer exogenous genes into human cells. The first type is the viral vector system and the second is the non-viral vector techniques. However, no effective systems are available. Referring to the non-viral system, it was reported in recent years that exogenous DNA could be transduced into cells by receptor-mediated gene transfer techniques. The exogenous DNA can form a complex with a ligand associated polypeptide. After the binding of ligand and cell receptor, the DNA/polypeptide can be endocytosed thereby transferring the exogenous gene into cells enriched with the relevant receptors. Wu G. Y. et al (J. Biol. Chem. 263:14621, 1988) described that asiologlycoprotein conjugated polylysine can mediate uptake of exogenous gene by hepatocytes. Transferrin was also used as a ligand to transduce exogenous genes into cells by binding with cell surface transferrin receptor and subsequent endocytosis (Birnstiel M. L. et al, PNAS, USA. 87:3410–3414, 1990).

However, the gene transduction by these receptor-mediated gene transfer system was limited to non-tumorous cells, such as hepatocytes, but not described to target malignant cells. One of the major limitations of these vectors or other non-viral systems is the enzymatic degradation of the endocytosed DNA due to the fusion of lysosome and endosome vesicles, thereby reducing the transduction efficiency and expression of exogenous genes. However, it is well known that some envelope domains of virus, such as adenovirus or influenza virus, can cause endosomolysis and release the endocytosed virus, to protect from the lysosomal fusion and degradation. It was reported that defective or chemically inactivated adenovirus can be used to disrupt the endosome so as to increase the transfer efficiency of the receptor-mediated gene transfer system (Birnstiel M. L., PNAS, USA. 89:6094–6098, 1992).

SUMMARY OF INVENTION

The present invention is a novel targeting gene transfer system for tumor gene therapy. The present system comprises a ligand oligopeptide for receptor recognition (LOP), a polycationic polypeptide(PCP) for DNA binding and an endosome-releasing oligopeptide (EROP) for endosome disrupting. This system includes the 3-element composite polypeptide vector LOP/PCP/EROP which can bind DNA to form a 4-element complex gene transfer system and 2-element composite polypeptide vector LOP/PCP which can bind DNA to form a 3-element complex gene transfer system. The LOP includes E5(14 amino acid) for IGF-I and IGF-II receptor, GE7(16 amino acid) for EGF receptor and GV1(32 amino acid), GV2(36 amino acid) for VEGF receptor recognition. The PCP includes protamine, polylysine and histone. The EROP is a synthetic 20 amino acid oligopeptide homologous to haemagglutinin domain of Influenza viral envelope (HA20). To take advantage of the recognition capability of LOP for receptor overexpressed on surface membrane of cancer cells, therapeutic genes are to be transduced into cells via endocytosis and endosomolysis for tumor gene therapy.

It is an object of the present invention to provide a new gene transfer system that can targetably transduce exogenous genes into certain type of cancer cells in vitro and in vivo with high efficiency. This system consists of following elements:

i. A receptor-specific ligand oligopeptide(LOP) that is designed to recognize the cells with relevant expressed receptor.
ii. A polycationic polypeptide (PCP) for forming a complex with DNA from plasmid containing exogenous gene. The PCP is polylysine, protamine or histone.
iii. An endosome-releasing oligopeptide (EROP) for the release of exogenous DNA from endosome after endocytosis.
iv. The polypeptide comprising of the above elements to form a complex with DNA from recombinant eukaryotic expression vector containing exogenous gene as a novel gene transfer system (GDS).

The other object of the present invention is to provide the system that comprises composite polypeptide vector:

i. LOP and EROP are together linked with PCP to form LOP-PCP-EROP 3-element composite polypeptide vector
ii. LOP and EROP are independently linked with PCP to form LOP-PCP and EROP-PCP 3-element composite polypeptide vector.

The other object of the present invention is to design and prepare the LOP E5, GE7, GV1 and GV2:

i. E5 is to recognize and bind specifically to IGF-I and IGF-II receptors that are highly expressed in human hepatic or breast cancer.
ii. GE7 is to recognize and bind specifically to EGF receptor or indirectly to c-erbB2, that are highly expressed in human hepatic, breast, gastric, esophageal, lung cancer and brain glioblastoma.
iii. GV1 and GV2 are to recognize and bind to vascular endothelial growth factor receptor(VEGF R), which are highly expressed in angiogenetic vessels in most solid malignant tumors.

The other object of the present invention is to use protamine, polylysine and histone as a backbone of the GDS to form a complex with DNA.

The other object of the present invention is to use the composite polypeptide LOP-PCP and EROP-PCP to bind DNA and form a LOP-PCP/EROP-PCP/DNA complex. DNA of exogenous genes include:

1. Antisense sequence of protooncogenes $ras^H$, $ras^K$, $ras^N$, c-myc, bcl-2 and growth factor receptor. The antisense sequence is either in a form of double stranded DNA or in a form of oligoribonucleotides or oligodeoxyribonucleotides.
2. Cancer suppressor gene p53 and Rb.
3. Suicide gene HSV-TK and CD.
4. Apoptosis-inducing gene p15, p16 and $p21^{WAF-1}$.
5. Cytokine gene GM-CSF, Interferon α and γ, Interleukin 2,3,4,12 and 15.

The other object of the present invention is to use the haemagglutinin domain oligopeptide HA20 as an element in GDS to break the endosome and prevent lysosomal degradation of transduced gene after endocytosis.

The HA20 is to be used either as a part of the covalently bound composite polypeptide, LOP-PCP/HA20-PCP to form a complex with DNA or as a free element used in conjunction with LOP-PCP/DNA complex.

The another object of the present invention is to utilize the GDS to transduce genes into cells either in vitro or in vivo for human tumor gene therapy.

DETAILED DESCRIPTION OF THE INVENTION

The present invention principally relates to 4 parts: providing ligand oligopeptides (LOP) for specific recognition and binding to cell growth factor receptors; providing a 2-element composite polypeptide vector LOP-PCP to form a 3-element gene transfer system composed of a complex of DNA from exogenous gene and LOP-PCP; providing a 3-element composite polypeptide vector LOP-PCP-EROP to form a 4-element gene transfer system composed of a complex of DNA from exogenous gene and LOP-PCP-EROP or LOP-PCP plus EROP-PCP; providing methods and techniques to transduce gene(s) into cells both in vitro and in vivo for tumor gene therapy.

1. The first part of the present invention is to provide the LOP E5, GE7, GV1 and GV2 for specific recognition and binding to insulin growth factor I and II receptor(IGF-I R and IGF-II R), epidermal growth factor receptor(EGF R) and vascular endothelial growth factor receptor(VEGF R) respectively.

It has been demonstrated that IGF-I R and IGF-II R are over-expressed in human hepatic cancer and other malignancies. EGF R is highly expressed in human hepatic, mammary, ovarian, gastric, cervix cancer, glioblastoma, lung adenocarcinoma, nasopharyngeal cancer etc. VEGF R is over-expressed in vascular endothelial cells of tumor blood vessels and some cancer cells. Based on the mechanism of growth factor ligand and its receptor recognition and binding, a series of LOPs for above-mentioned receptors are designed and synthesized by using Peptide Synthesizer 430(ABI). The procedures of oligopeptide synthesis are according to the manufacturer's manual. The LOP products are purified by high pressure liquid chromatography and lyophilized. The product quality has been confirmed by amino acid analysis.

Synthesis of 4-element complex gene transfer system was performed and then subjected to biological and screening analysis. First of all, LOP and PCP (polylysine, protamine or histone) were independently reacted with SPDP(N-esuccinimidyl-3-2-pyridyl-dithiopropionate) to produce LOP-3-(2-pyridyldithio)-propionate (LOP-PDP) and PCP-PDP. PCP-PDP was then converted into PCP-$(SH)_2$ and form LOP-PCP composite polypeptide vector with LOP-PDP by disulfide covalent bond. FIGS. 1–3 indicated the Sephadex G50 chromatography purification of E5-polylysine, GE7-polylysine and GV2-protamine conjugates respectively. The first peak was collected as the purified product. FIGS. 4 and 5 demonstrated the results of amino acid composition analysis of the hydrolyzate of E5-oligopeptide and GE7-polylysine. Using the same method, EROP(HA20)-PCP was prepared. A 4-element DNA/polypeptide gene transfer system composed of LOP-PCP/EROP-PCP/DNA was prepared based on the electrostatic binding between negative charge of DNA and the positive charge of PCP in the 3-element composite polypeptide vector LOP/PCP/EROP. Using β-galactosidase(pSV-β-gal) as an exogenous gene, the transition of LOP-PCP/HA20-PCP/β-gal into human hepatoma cells was performed in vitro and the transduction efficiency was examined by X-gal(5-bromo-4-chloro-3-indolyl-β-D-galactoside) cytochemistry analysis. E5, GE7, GV1 and GV2 were proved to be effective LOPs for receptors IGF-I R and IGF-II R, EGF R and VEGF R respectively. These receptors were either highly expressed in cancer cells or in tumor vascular endothelial cells. FIGS. 6–8 were the results of agarose electrophoresis of E5, GE7, GV1 and GV2 4-element gene transfer system respectively, indicating DNA migration retarded by polypeptide as a stable complex. FIGS. 9–12 illustrated the results of E5 4-element gene transfer system to transduce β-gal gene into human hepatoma cell line SMMC-7721 revealed by X-gal(blue granules in cells). In contrary, E5 system can not transduce β-gal gene into normal hepatocyte cell line L02 or normal primary culture hepatocyte R02, similar to PBS control(no blue granules in cells). GE7 4-element system can transduce β-gal gene into human hepatoma BEL-7402 (FIG. 13) and GV2 system transduced β-gal gene into tumor vascular endothelial cells (FIG. 14).

Based on the biological screening assay, the LOPs in the present invention are E5(amino acid sequence, EPFRS PDLAL ETYG), (SEQ ID NO.1) GE7(NPVVG YIGER PQYRD L), (SEQ ID NO.2) GV1(CHPIE TLVDI FQEYP DEIEY IFKPS PVPLM RP), (SEQ ID NO.3) GV2(PVPTE ESNIT MQIMR IKPHQ GQHIG EMSFL QHNKC E), (SEQ ID NO.4).

Any oligopeptides that possess similar immuogenic epitopes with E5, GE7, GV1 and GV2 oligopeptides to react with antibodies against the above mentioned oligopeptides and that can bind with IGF-I R, IGF-II R, EGF R and VEGF R is adapted to the present invention. Any oligopeptides that some of the amino acids of the above mentioned oligopeptides were replaced by similar amino acids in corresponding site but not affecting their ability to bind the receptor is also adapted to the present invention.

The LOP E5, GE7, GV1 and GV2 mentioned above can be in the form of nucleotide sequence, used to construct a recombinant expression vector for the purpose of construction of a gene transfer system LOP/PCP/HA20 or to construct a hybrid gene with toxin or cytokine for therapeutic use.

The present invention is also to use LOPs mentioned above to recognize and bind to receptor(s) that are highly expressed in hemopoietic cells, macrophage, lymphocytes, hepatic, renal, endothelial, neural and cardiac muscle cells and to use these LOP to construct LOP-PCP/HA20-PCP for transducing exogenous gene into the above mentioned relevant cells for gene therapy of cancer or non-cancer disease.

2. The second part of the present invention is to provide a 2-element composite polypeptide vector LTOP-PCP to form a 3-element complex gene transfer system as a complex of LOP-PCP and DNA from exogenous gene. The LOP includes E5, GE7, GV1 and GV2; PCP includes protamine, polylysine or histone. DNA exogenous genes include cancer suppressor gene, suicide gene, apoptosis-inducing gene, cytoktine gene and antisense sequences of protooncogens constructed in an eukaryotic expression vector driven by SV40 or CMV promotors, or constructed in recombinant retrovirus or adenovirus. Antisense sequences include those derived from protooncogens ($ras^H$, $ras^K$, $ras^N$, c-myc, bcl-2), growth factors and their receptor genes. Antisense sequence relate either to DNA construct of a complete or part of the cDNA, or to single-stranded oligonucleotides. Cancer suppressor genes include p53 and Rb. Suicide genes include HSV-TK(Herpes simplex thymidine kinase), CD(cytosine deaminase)genes. Apoptosis-inducing genes include p15, p16, and p21$^{WAF-1}$. Cytokine genes include GM-CSF (Granulocyte Macrophage Colony Stimulating Factor), TNF α (Tumor necrosis factor α), IFN(Interferon) α, γ, IL(Interleukin) 2,3,4,12,15 gene. The preparation of DNA/LOP-PCP is similar to that described in the previous section(Part 1). LOP is covalently linked to PCP (protamine, polylysine or histone) to form LOP-PCP. DNA and LOP-PCP are electrostatically bound to form a LOP-PCP/DNA complex as a 3-element complex gene transfer system.

3. The third part of the present invention is to provide a 3-element composite polypeptide vector of LOP-PCP-EROP to form a 4element complex gene transfer system as a complex of LOP-PCP-EROP and DNA from exogenous gene. The present invention also provides a 3-element composite vector as LOP-PCP polypeptide plus EROP-PCP polypeptide to form a 4-element complex with DNA as LOP-PCP/EROP-PCP/DNA. The presence of EROP in the vector increases the transduction and expression efficiency of exogenous gene. EROP in the present invention is to take a synthetic oligopeptide HA20 homologous to the haemagglutinin domain of Influenza virus. The synthesis of HA20 refers to literature (Midoux P. Nucleic Acid Res., 21:871,1993). HA20 is a 20 amino acid oligopeptide with its sequence as GLFEA IAEFI EGGWE ELIEG, (SEQ ID NO.5).

The first step of preparation of the 4-element gene transfer system is to covalently link LOP with PCP (protamine, polylysine or histone), by using coupling reagent SPDP. Then, HA20 is covalently linked the LOP-PCP to form LOP-PCP-HA20 3-element composite polypeptide vector. The LOP-PCP-HA20 is mixed and reacted with DNA from exogenous gene to form a complex of LOP-PCP-HA20/DNA by electrostatic binding. By similar method, HA20 is linked with PCP(polylysine, protamine or histone) to form HA20-PCP. LOP-PCP and HA20-PCP are mixed according to certain molar ratio and react with DNA from exogenous gene to form a LOP-PCP/HA20-PCP/DNA complex by elecrostatic binding. FIGS. 6,7,8 demonstrated results of agarose gel electrophoresis of the E5, GE7, GV1 and GV2 4-element LOP-PCP/HA20-PCP/DNA gene transfer systems, respectively, indicating the migration retardation of the stable complex. HA20-PCP can be mixed with LOP-PCP and reacted with DNA from exogenous gene to form 4-element complex gene transfer system LOP-PCP/HA20-PCP/DNA. In addition, HA20 oligopeptide can be used by mixed with LOP-PCP/DNA. All these preparation can increase the gene transfer efficiency.

The 4-element gene transfer system is also adapted for using two or more than two different types of LOP in LOP-PCP/HA20-PCP system to form complex with DNA from exogenous gene or recombinant virus. In addition, it is also adapted for using 4-element system of same type of LOP to form a complex with DNA or recombinant virus derived from two or more than two different types of exogenous genes for the purpose of cancer gene therapy.

The 3-element complex gene transfer system is further to use the 2-element composite polypeptide vector LOP-PCP to form a conjugate with recombinant virus for gene therapy. The recombinant virus includes genetic engineered adenovirus or retrovirus containing exogenous genes. Recombinant viruses can be either in a conjugated or non-conjugated form in the 3-element gene transfer system. The genes in recombinant viruses include suicide gene HSV-TK, CD; apoptosis-inducing gene p15, p16, p21$^{WAF-1}$; cancer suppressor gene p53, RB; cytokine gene GM-CSF, TNF α, INF α, γ, IL 2, 3, 4, 12, 15; antisense sequence of protooncogene ras$^H$, ras$^K$, ras$^N$, c-myc, bcl-2; antisense sequence of growth factor and receptor gene, IGF-I, IGF-II, EGF, IGF-I R, IGF-II R, EGF R. The present system can also use defective virus that does not contain any exogenous gene. The present system can also apply in antisense oligoribonucleotides or oligodeoxyribonucleotides.

The above mentioned 3-element polypeptide LOP/PCP/EROP can be produced by genetic engineering techniques by constructing a recombinant DNA expression plasmid that encodes the amino acid sequence of HA20, PCP and EROP, thus facilitating the industrial production of vector system of well-controlled quality.

4. The forth part of the present invention is to apply the 3-element LOP/PCP/EROP composite polypeptide vector and its capability to form DNA/polypeptide gene transfer system in gene transfer both in vitro and in vivo for tumor gene therapy.

In vitro Experiment

1) In vitro gene transfer E5-polylysine/HA20-polylysine/β-gal 4-element complex gene transfer system has been applied to transduce β-gal gene into human hepatoma cell line SMMC-7721, normal hepatocyte line L02 and normal primary culture hepatocyte R02. Results indicated that β-gal gene was transferred into hepatoma cells mediated by the 4-element gene transfer system with high efficacy and targetability (FIGS. 9–12). As control, β-gal DNA alone. E5-polylysine/β-gal 3-element complex, HA20-polylysine/β-gal 3-element complex, polylysine/β-gal and PBS were also used for transfection IGF-I R and IGF-II R positive SMMC-7721 cells. The transduction efficacy and targetability were evaluated by X-gal stain. Results were illustrated in Table 1–3.

TABLE 1

Transduction efficiency of pSV-β-gal gene mediated by various polypeptide/DNA complexes in human hepatoma SMMC-7721 cells

| Groups | PBS | β-gal DNA | P/β-gal | E5-P/β-gal | HA20-P/β-gal | E5-P/HA20-P/β-gal |
|---|---|---|---|---|---|---|
| Percentage of β-gal positive cells | 0% | 0% | 0.1% | 10% | 0.2% | 60% |

PBS: Phosphate buffered saline as control
β-gal DNA: pSV β-gal DNA alone
P/β-gal: polylysine/pSV β-gal DNA
E5-P/β-gal: E5-polylysine/pSV β-gal DNA
HA20-P/-gal: HA20-polylysine/pSV β-gal DNA
E5-P/HA20-P/β-gal: E5-polylysine/HA20-polylysine/pSV β-gal DNA The transduction efficiency of the complex derived from different elements was shown in table 1. The 4-element system can transduce β-gal gene into hepatoma SMMC-7721, but not into normal human hepatocyte line L02 and primary culture hepatocyte R02 (Table 2). Table 3 illustrated that β-gal into SMMC-7721 cells can be detected at 48 hr after transduction and reached the peak at 72 hr.

TABLE 2

Transduction of pSV-β-gal gene into human hepatoma SMMC-7721, hepatocyte line L02 and primary culture hepatocytes R02, mediated by E5-polylysine/HA20-polylysine/pSV β-gal DNA complex system

| Cell type | Transduced gene | Percentage of β-gal positive cells (%) |
|---|---|---|
| SMMC-7721 | (PBS) | 0 |
| SMMC-7721 | PSV-β-gal | 60 |
| L02 | PSV-β-gal | 0.1 |
| R02 | PSV-β-gal | 0.1 |

TABLE 3

Time course of β-galactosidase gene expression after transfection in vitro in human hepatoma SMMC-7721 cells mediated by E5-polylysine/HA20-polylysine/pSV-β-gal DNA

| Time after transfection (hr) | 24 | 48 | 72 | 96 |
|---|---|---|---|---|
| Expression of β-galactosidase gene in SMMC-7721 cells | − | + | +++ | − |

GE7-polylysine/HA20-polylysine/β-gal or GE7-protamine/HA20-protamine/β-gal 4-element gene transfer system was used to transfer β-gal gene into different types of human cancer cell lines in vitro, including human hepatoma SMMC-7721 and BEL-7402, glioblastoma U87, mammary cancer Bcap-37, ovarian cancer 3A0 and A0, pulmonary adenocarcinoma SPC-A1. Normal hepatocyte L02 and mouse NIH/3T3 were used as control. As illustrated in FIGS. 13 and 15–22, β-gal gene was transduced by GE7 4-element gene transfer system into EGF R positive cell lines: BEL-7402, SMMC-7721, U87, Bcap-37, 3A0,A0, SPC-A1 revealed b X-gal stain. GE7 4-element system failed to transduce β-gal gene into EGF R negative cell line L02 or NIH/3T3, as no blue granules were observed by X-gal. β-gal gene can not be efficiently transduced into EGF R positive BEL-7402 by 3-element complex HA20-polylysine/β-gal, 2-element complex polylysine/β-gal or β-gal naked DNA(FIGS. 23–25).

10% (FIG. 26). Taking naked β-gal DNA, 3-element complex GE7-polylysine/β-gal, HA20-polylysine/β-gal, 2-element complex polylysine/β-gal and PBS as control, the efficiency of the gene transfer system was examined on EGF R positive cell line BEL-7402 with X-gal histochemical stain. The result was listed in Table 4 and 5. The transduction efficiency of GE7 4-element complex to different cell line and the transduction efficiency of the complex composed of different elements to hepatoma cell line BEL-7402 was demonstrated in Table 4. The transduction efficiency of GE7 4-element system in transferring β-gal gene into hepatoma versus normal hepatocytes and mouse NIH/3T3 was illustrated in Table 5. In Table 6, it was demonstrated that β-gal gene expression initiated at 24 hr after transduction and reaches its peak at 168 hr in BEL-7402 mediated by GE7 4-element system.

TABLE 5

Transduction efficiency of β-galactosidase gene in hepatocyte line L02 and mouse fibroblast NIH/3T3 mediated by GE7 4-element gene transfer system

| Cell line | L02 | NIH/3T3 |
|---|---|---|
| *Transduction efficiency | <0.1 | <0.1 |

*Transduction efficiency was denoted as the percentage of β-gal (+) cells, based on the average value of 3 experiments.

TABLE 6

Time course of β-gal gene expression after transfection in human hepatoma BEL-7402 mediated by GE7 4-element complex gene transfer system

| Time (hr) | 24 | 48 | 72 | 96 | 120 | 144 | 168 |
|---|---|---|---|---|---|---|---|
| Expression level | + | + | ++ | ++ | +++ | +++ | ++++ |

1) In vitro transduction efficacy of apoptosis-inducing genes, $p21^{WAF-1}$, p16 and p15 to inhibit growth of human hepatoma cells mediated by E5 4-element gene transfer system.

E5-polylysine/HA20-polylysine/$p21^{WAF-1}$ system was added into medium of cultured human hepatoma SMMC-

TABLE 4

Transduction efficiency of pSV-β-gal gene mediated by different complex gene transfer system

| | *Percentage of β-gal (+) cells in different cell lines | | | | | | |
|---|---|---|---|---|---|---|---|
| Complex | BEL-7402 | SMMC-7721 | SPC-A1 | Bcap-37 | 3AO | U87 | AO |
| PBS control | 0 | — | — | — | — | — | — |
| β-gal | 0 | — | — | — | — | — | — |
| P/β-gal | <0.1 | — | — | — | — | — | — |
| GE7-P/β-gal | <10 | — | — | — | — | — | — |
| HA20-P/β-gal | <0.1 | — | — | — | — | — | — |
| GE7-P/HA20-P/β-gal | >90 | >80 | >80 | >80 | >65 | >30 | >15 |

β-gal DNA: pSV-β-gal DNA
P/β-gal: polylysine/pSV-β-gal DNA
GE7-P/β-gal: GE7-polylysine/pSV-β-gal DNA
HA20-P/β-gal: HA20-polylysine/pSV-β-gal DNA
GE7-P/HA20-P/β-gal: GE7-polylysine/HA20-polylysine/pSV-β-gal DNA
"—" not tested
*The number was based on the average value of three experiments The transduction rate of β-gal into BEL-7402 cells by GE7 3-element system(GE7-polylysine/β-gal) was less than 7721 cells for 72 hr. After fixed with acetone, cells were stained with DAPI to examine the cell nuclear structure. As shown in FIG. 27, chromatin condensation, nuclear pyknosis and fragmentation as characteristic features for apoptosis, were observed. Using in situ terminal end-labeling techniques by Boehringer Mannheim Kit, apoptosis was obviously detected as shown in FIGS. 28 and 29. At 96 hr. after transfection, apoptosis was observed in 15% of cells mediated by $p21^{WAF-1}$ E5 4-element system; negative results were observed in control without $p21^{WAF-1}$. Results of growth inhibitory effect on 7721 cells by E5 4-element system containing $p_{21}^{WAF-1}$, p16 and p15 gene were demonstrated by the growth curve of cells cultured in 24 well-plate and counted at 2 day intervals(FIG. 30).

The GE7-polylysine/HA20-polylysine/$p21^{WAF-1}$ 4-element gene transfer system was used to transduce human hepatoma BEL-7402 cells. 5 and 7 days after transfection, DNA was isolated from cells, both the suspended and adhered, and analyzed in 1.5% agarose gel electrophoresis. DNA ladder was observed in the transduced group, but not in the control, indicating that apoptosis was induced by $p21^{WAF-1}$ gene transduced into the hepatoma cells. Using the same system, cell counts were performed at day 1, 2,3, 4, 5, 6, 7, 8 after transfection. Results indicated that $p21^{WAF-1}$ can effectively inhibit the growth of hepatoma cells mediated by the GE7-polylysine/HA20-polylysine/$p21^{WAF-1}$ 4-element system. The growth curve was demonstrated in FIG. 31, with PBS as control.

In vivo Experiment

1) In vivo gene transduction E5-polylysine/HA20-polylysine/β-gal 4-element gene transfer system was used to transduce gene into human tumor in vivo. Human hepatoma SMMC-7721 was transplanted subcutaneously in nude mice. The above system was administrated by injection subcutaneously around the tumor. Animals were sacrificed at 12, 24, 48, 60,72 and 96 hr after treatment. Tumors were dissected and stained with X-gal. Results demonstrated that β-gal expression was observed at 12 hr, reached its peak at 24 hr and decreased from 48 hr. Expression was still detected at 96 hr (FIG. 32).

GE7-polylysine/HA20-polylysine/β-gal system was administrated in the same way into different human tumors subcutaneously implanted in nude mice. The human tumors included hepatoma SMMC-7721, BEL-7402, brain glioma U251, breast cancer Bcap-37, ovarian cancer 3A0, lung adenocarcinoma SPC-A1, colon cancer LOVO, gastric cancer SGC, lung small cell carcinoma H128 and cervical cancer xenograft. Animals were sacrificed at 4, 8, 12, 24 hr, day 2, 4, 7, 15, 20, 30 and 40. Tumors were dissected then and stained with X-gal. Results were illustrated in FIG. 33, indicating that β-gal gene can be effectively transduced into all above human tumors except H128 which has been proved to be negative for EGF R. FIGS. 34 to 42 illustrated the results of histochemistry examination of β-gal expression in these human cancer. Positive results were observed in all these human tumors (FIGS. 34–41) except H128 (FIG. 42).

GV2-protamine(or histone)/HA20-protamine/β-gal 4-element gene transfer system was injected under microscope into portal vein of nude mice in which human hepatoma was intrahepatically transplanted. Animals were sacrificed at day 14 after treatment. Tumors were dissected and stained with X-gal. The frozen section were counter-stained with Fast Nuclear Red and examined under microscope. β-gal gene expression was observed in endothelial cells in capillaries and small blood vessels in tumor, particularly in regions close to necrosis lesion inside the tumor. β-gal expression was also detected in some infiltrating cancer cells(FIG. 43). Low level of expression of β-gal gene has been detected in endothelial cells of large blood vessels. No β-gal expression was detectable in normal liver cells. GV2-protamine/HA20-protamine/β-gal was also injected into hepatoma that was implanted subcutaneously in nude mice. Tumor was dissected from animals sacrificed two days later and stained with X-gal. Histochemical study of frozen section demonstrated that β-gal was expressed in endothelial cells of capillaries and small blood vessels of tumor(FIG. 44), but not in liver cells.

2) Efficacy test of inhibition of tumor growth in vivo by transduction of $p21^{WAF-1}$.

Human hepatoma SMMC-7721 was subcutaneously implanted in nude mice. After tumor size reached about 0.5 cm, animals were randomly divided into different groups, 6 mice per each. Animals received treatment of injection of E5-polylysine/HA20-polylysine/$p21^{WAF-1}$ or E5-polylysine/HA20-polylysine around tumor twice per week, for two weeks. The dose per injection was equivalent the complex containing 20 µg of plasmid $p_{21}^{WAF-1}$ DNA. Animals were sacrificed 3 weeks after treatment. Tumors were dissected, weighed and their size was measured. Results were summarized in Table 7 and FIG. 45, indicating a significant inhibitory effect on growth of hepatoma by transduction of $p21^{WAF-1}$ in vivo, mediated by E5-plylysine/HA20-polylysine/$p21^{WAF-1}$ system as compared with the E5 3-element system in terms of the tumor volume and weight (Table 7).

TABLE 7

Growth inhibitory effect of $p21^{WAF-1}$ on human hepatoma SMMC-7721 in nude mice mediated by E5-polylysine/HA20-polylysine/$p21^{WAF-1}$ 4-element complex gene transfer system

| Groups | Tumor volume (cm³) | Tumor weight (g) |
| --- | --- | --- |
| E5 vector system without $p21^{WAF-1}$ DNA | 0.85 ± 0.05 | 0.23 ± 0.06 |
| E5-polylysine/HA20-polylysine/$p21^{WAF-1}$ DNA | 0.2 ± 0.06 | 0.55 ± 0.02 |
| Inhibition rate | 75.3% | 76.1% |
| P value | <0.05 | <0.02 |

As no inhibitory effect on tumor growth was observed in groups treated with E5-polylysine/$p21^{WAF-1}$, E5-polylysine/HA20-polylysine, HA20-polylysine/$p21^{WAF-1}$, polylysine/$p21^{WAF-1}$ and $p21^{WAF-1}$ DNA alone, it was demonstrated that E5-polylysine/HA20-polylysine/$p21^{WAF-1}$ 4-element complex gene transfer system can effectively deliver exogenous gene into hepatoma cells in vivo and significantly inhibit the growth of hepatoma in vivo.

Using the same nude mice model with subcutaneously transplanted human hepatoma, GE7-polylysine/HA20-polylysine/$p21^{WAF-1}$ 4-element complex system was injected subcutaneously at the site surrounding the tumor after it reached the size of 0.5 cm in diameter. The dose per mouse was the amount of complex containing 0.2 µg $p21^{WAF-1}$ DNA, one injection only. Normal saline, GE7-polylysine/HA20-polylysine polypeptide and $p21^{WAF-1}$ DNA alone were injected as control. Animals were sacrificed two weeks after treatment. The weight and volume of the dissected tumors were measured. Results indicated the significant inhibitory effect of the $p21^{WAF-1}$ gene mediated by GE7 4-element gene transfer system on growth of human hepatoma in vivo(FIG. 46, Table 8 and 9). Table 8 and 9 demonstrated the inhibitory effect was significant based on both the data from measurement of tumor volume(Table 8) and weight(Table 9), thereby indicating that exogenous gene can be effectively target to transplanted human hepatoma and inhibit the growth of hepatoma cells in vivo.

According to the ability of the polypeptide vector system to bind the recombinant virus containing various types of exogenous genes, the present invention possesses the potential applicability to use multiple exogenous genes in gene therapy.

Based on the presented experimental data, the present invention possesses the capability to target DNA of exogenous gene(s) into tumor cells both in vitro and in vivo to inhibit the growth of tumor, thereby indicating a broad potential in cancer gene therapy.

TABLE 8

In vivo inhibitory effect of $p21^{WAF-1}$ on human hepatoma transplanted in nude mice mediated by E5-polylysine/HA20-polylysine/$p21^{WAF-1}$ DNA

| Groups | Tumor volume $\overline{V} \pm SD$ (cm³) | *Inhibition rate (%) | P |
|---|---|---|---|
| Normal saline control | 1.253 ± 0.497 | | |
| P21$^{WAF-1}$ DNA alone | 1.000 ± 0.280 | 20.19 | >0.1 |
| GE7-polylysine/HA20-polylysine | 2.253 ± 1.406 | −102.81 | >0.05 |
| GE7-polylysine/HA20-polylysine/p21$^{WAF-1}$ | 0.164 ± 0.091 | 86.91 | <0.02 |

*The inhibition rate was based on the average value of 3 experiments with the normal saline group as control

TABLE 9

Inhibitory effect of $p21^{WAF-1}$ on human hepatoma transplanted in nude mice mediated by different complexes

| Groups | Tumor weight $\overline{W} \pm SD$ (g) | *Inhibition rate % | P |
|---|---|---|---|
| Normal saline | 0.663 ± 0.160 | | |
| P21$^{WAF-1}$ DNA alone | 0556 ± 0.130 | 16.22 | >0.1 |
| GE7-polylysine/HA20-polylysine | 0.169 ± 0.501 | −76.24 | >0.05 |
| GE7-polylysine/HA20-polylysine/p21$^{WAF-1}$ DNA | 0.129 ± 0.354 | 80.64 | <0.001 |

*The inhibition rate was based on the average value of 3 experiment with normal saline group as control

Advantages of the Present Invention

The novelty of the present invention was as following:
1. It is the gene transfer system firstly described in utilizing ligand oligopeptide(LOP) constructed in a 2-element or 3-element composite polypeptide vector to target exogenous genes to cancer cells or tumor vascular endothelial cells in which certain types of receptors are overexpressed.
2. It is a first description to use protamine as a polycationic polypeptide(PCP) backbone to form a complex with DNA and to use the endosome releasing oligopeptide HA20 as a component of composite polypeptide vector system.
3. It is a first description to integrate the LOP, PCP and EROP to construct a composite polypeptide vector that has effectively targeted exogenous genes to cancer cells and significantly inhibited the growth of cancer cells both in vitro and in vivo.

The present invention provides a set of LOP including E5, GE7, GV1 and GV2 for constructing LOP/PCP 2-element composite polypeptide vector to form a 3-element complex with DNA of exogenous gene, and for constructing LOP/PCP/EROP 3-element composite polypeptide vector to form a 4-element complex with DNA of exogenous gene as a gene transfer system. The presence of EROP can effectively increase the transduction efficiency. The HA20, a homologue of Influenza hemagglutinin, can be used as an EROP either in its free form or in a conjugated form covalently linked to PCP.

The present invention provides a novel non-viral vector system to target DNA of exogenous gene to cancer cells both in vitro and in vivo and to kill cancer cells but not the adjacent and distant normal cells. Its high efficiency and targetability makes it possible to transduce exogenous gene to cancer cells for treatment of cancer.

The present invention can transduce DNA of the exogenous gene with a size from 10 to $10^4$ nucleotides, thereby breaking through the size limitation of exogenous gene transduction by viral vectors, particularly for transferring large DNA sequences containing inducible regulatory sequence, multiple genes and genes of unusual size. The potential application of the present vector system to bind with recombinant virus is to further explore the area of application.

The present invention is to use one type of LOP-containing 3-element composite polypeptide vector to target two or more types of exogenous genes for multiple gene therapy.

The present invention is also to use two or more types of LOP 3-element composite polypeptide vectors to target one type of exogenous gene for further enhancing the efficiency of gene transduction into cancer cells.

In addition, the present invention is to construct a recombinant DNA expression vector, which containing the coding sequence of LOP/PCP/EROP. The polypeptide expressed in E. Coli, yeast or mammalian cells is feasible for large-scale industrial production.

Furthermore, the present invention is also adaptable to transduce exogenous genes to hemopoietic, lymphoid, liver, kidney, nerve cells with specific LOP, which can recognize the relevant receptors expressed in these cells for gene therapy of diseases including cancer, genetic, cardiovascular, neural, renal diseases and liver function failure.

EXAMPLES

Figure 1:
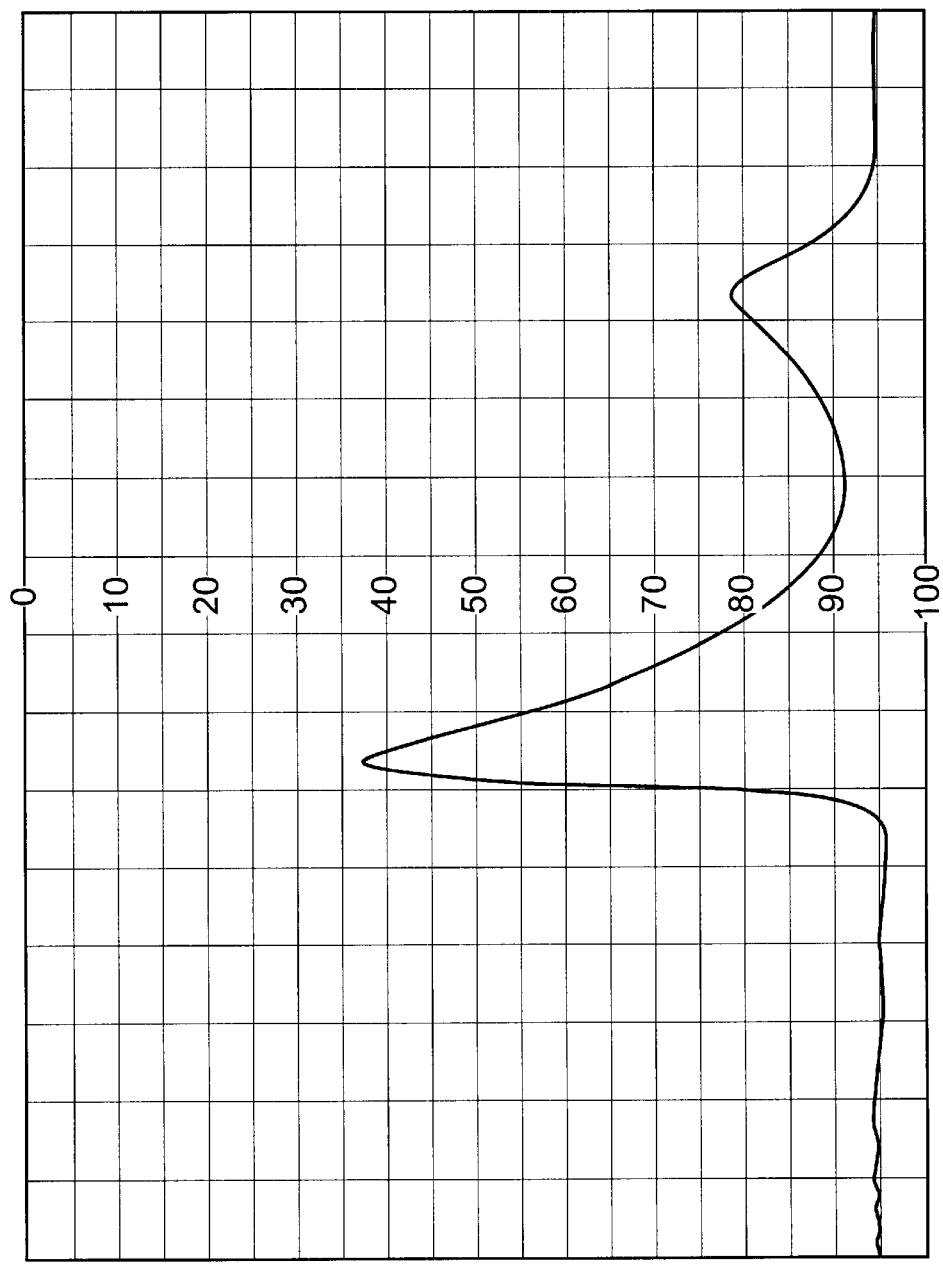
FIG. 1: The purification of E5-Polylysine conjugate after sephadex G50 column chromatography. The first peak is the conjugate.
Figure 2:
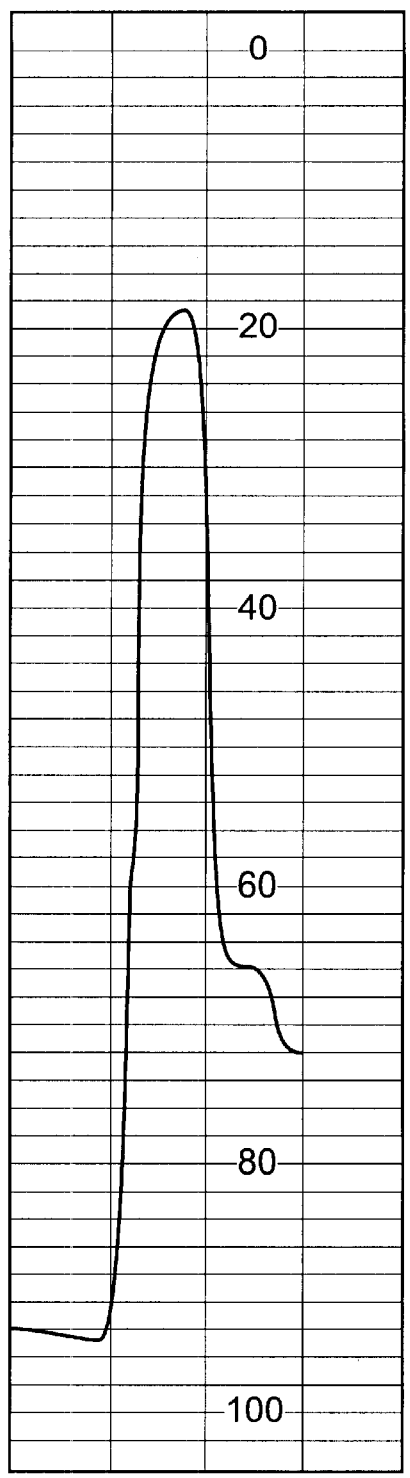
FIG. 2: The purification of GE7-Polylysine conjugate after Sephadex G50 column chromatography. The first peak is the conjugate.
Figure 3:
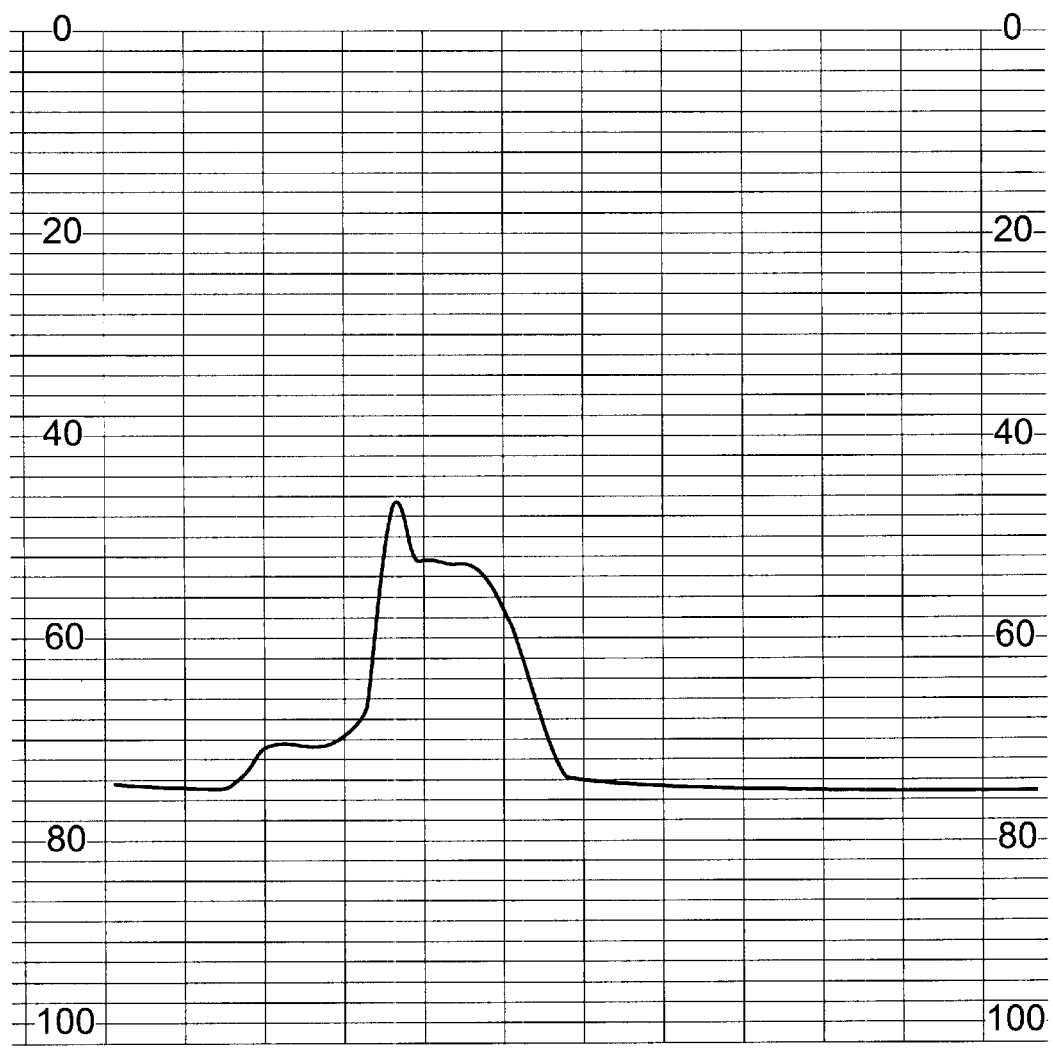
FIG. 3: The purification of GV2-Protamine conjugate after Sephadex G50 column chromatography. The sharp peak is the conjugate.
Figure 4:
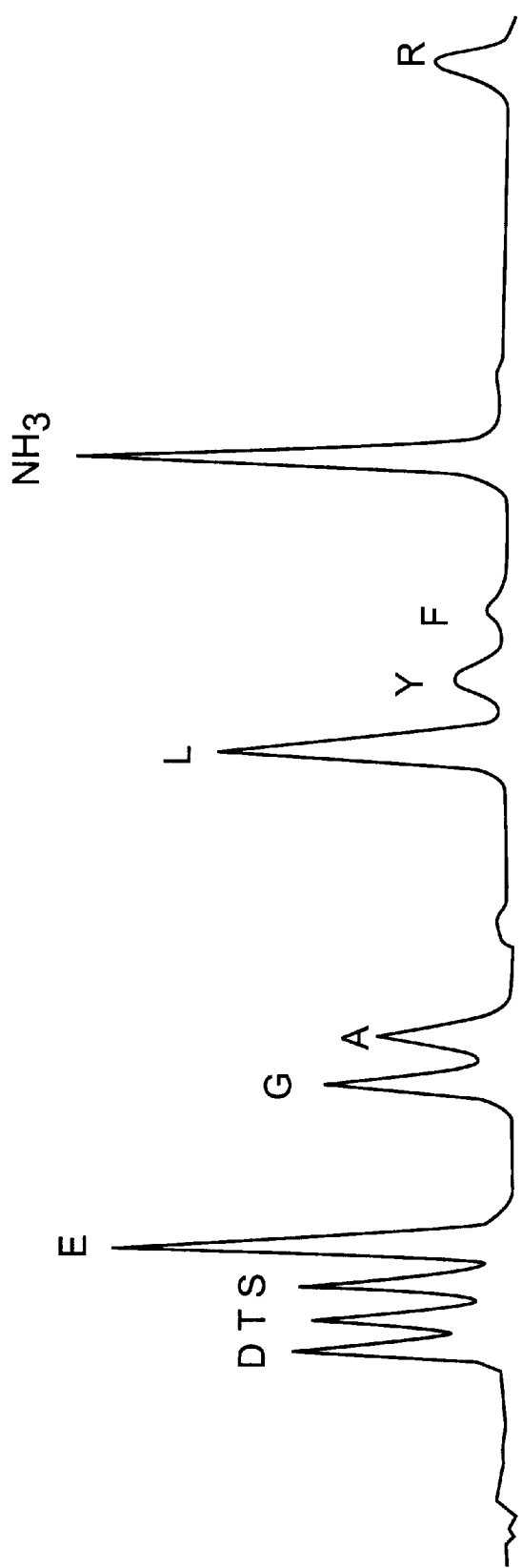
FIG. 4: The amino acid composition analysis of E5 oligopeptide after hydrolysis. D indicates aspartic acid; T, threonine; S, serine; E, glutamic acid; G, glycine; A, alanine; L, Lucine; Y, tyrosine; F, phenylalanine; R, arginine.
Figure 5:
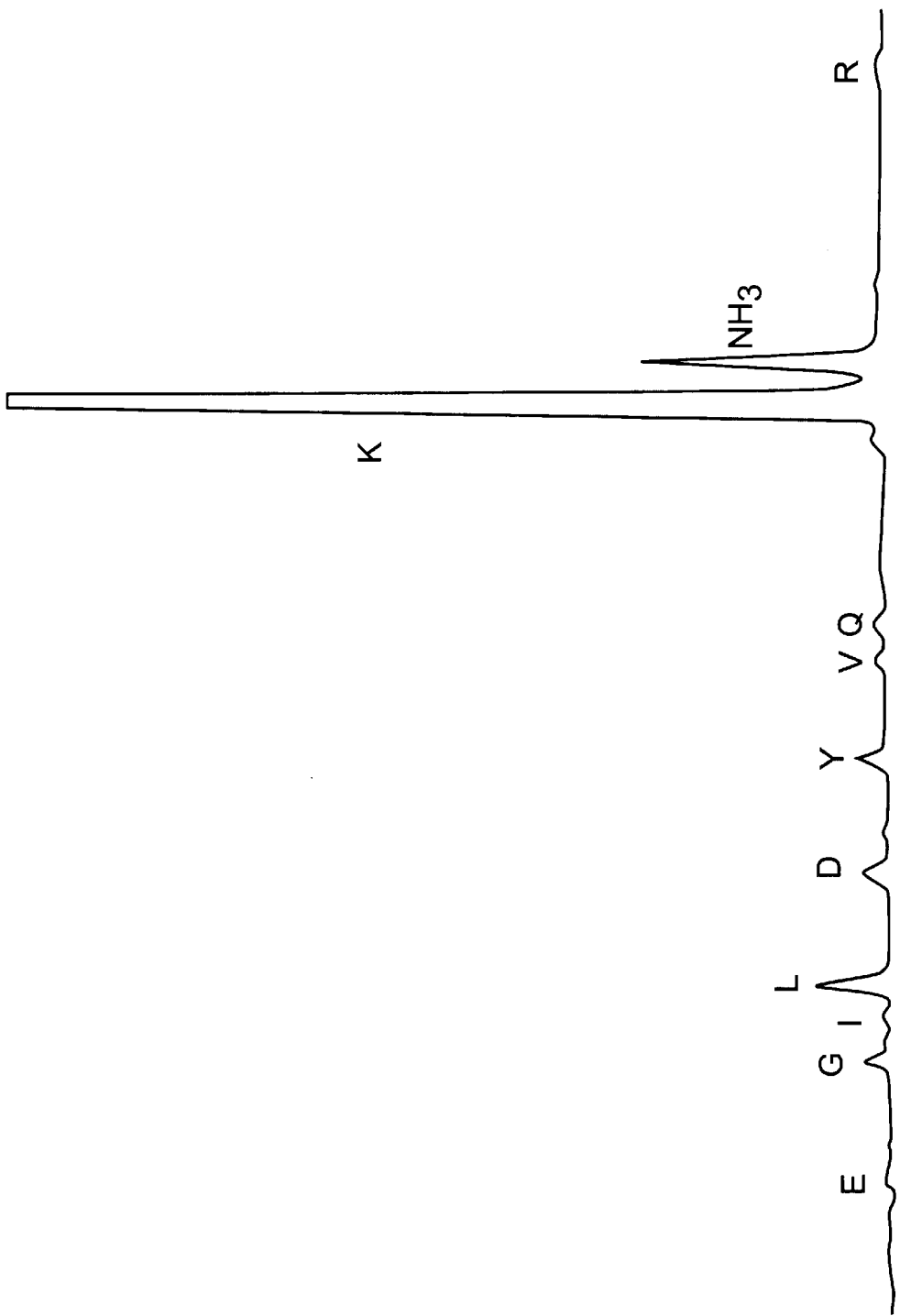
FIG. 5. The amino acid composition analysis of GE7-Polylysine conjugate after hydrolysis. E indicates glutamic acid; G, glycine; L, lysine; D, aspartic acid; Y, tyrosine; V, valine; Q, glutamine; K, Lysine; R, arginine.
Figure 6:
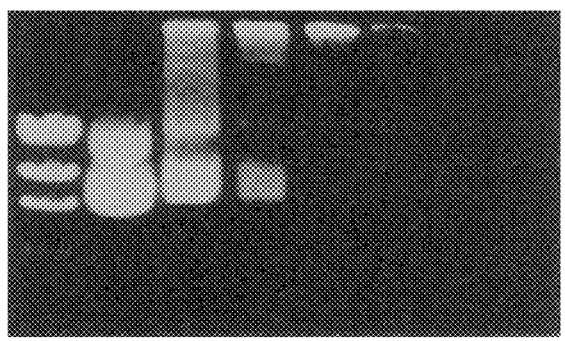
FIG. 6. Gel retardation analysis of E5 4 element complex by 1% agarose gel electrophoresis. M is the λ DNA Hind III digest marker; O, DNA alone; 1,2,3,4,5, the complex containing a W/W ratio of DNA to polypeptide at 2.4:1, 2:1, 1.4:1, 1:1, 0.5:1 respectively. The arrows indicate the DNA-polypeptide complex (upper) and the free DNA (lower).
Figure 7:
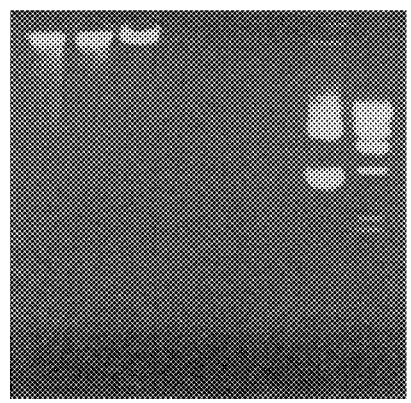
FIG. 7. Gel retardation analysis of the GE7-4 element complex by 1% agarose gel electrophoresis. 1,2,3,4,5,6 indicate the complex containing a W/W ratio of DNA to polypeptide at 2.2:1, 2.0:1, 1.8:1, 1.7:1. 1.6:1, 1.5:1 respectively. 7 is the DNA alone; 8, the λ DNA Hind III digest marker. The arrows indicate the complex (upper) and the free DNA (lower).

1. Example 1
Synthesis of Oligopeptide E5
Oligopeptide E5 was synthesized with solid phase peptide synthesizer(ABI 430) according to protocols from the manufacturer.
1.1. Oligopeptides were synthesized by chemical methods using solid phase peptide-synthesizer(ABI 430). The PAM amino acid resins were used as carrier-resin provided by ABI. The amino acid resin used for each reaction was 0.5 mmol, and amino acid 2 mmol. Amino acids were added sequentially according to the amino acid sequence of oligopeptide E5.

1.2. Cleavage of resin after synthesis of oligopeptide-resin in solid phase was carried out by utilizing 1 ml trifluoromethyl sulfonic acid (TFMSA) and 10% trifluoroacetic acid (TFA), stirred at room temperature for 2 hr. the crude product (about 300–350 mg) was precipitated with 250 ml anhydrous ethylether after removal of resin by filtration.
1.3. Desalting of the crude product was performed by Sephadex G10 column chromatography, eluted with 0.1 N glacial acetic acid. The first peak was dissolved in small amount of distilled water and lyophilized.
1.4. HPLC purification of the product was carried out by C8 reverse chromatography column (250 mm, diameter of 10 mm) provided by Beckman Inc. and monitored by UV detector (Beckman 420). The final product was collected and lyophilized.

2. Example 2
Synthesis of Oligopeptide GE7
All procedures were same as Example 1 except that amino acids were sequentially added according to the peptide sequence of oligopeptide GE7.

3. Example 3
Synthesis of Oligopeptide GV1 and GV2
All procedures were same as Example 1 except that amino acids were sequentially added according to the peptide sequence of oligopeptide GV1 and GV2.

4. Example 4
Preparation of Polypeptide $(LOP)_2$-PCP,$(EROP)_2$-PCP and $(LOP)_2$-PCP-$(EROP)_2$
LOP: ligand oligopeptide,
PCP: Polycationic polypeptide,
EROP: Endosome release oligopeptide.
4.1. Preparation of $(LOP)_2$-PCP
$(LOP)_2$-PCP was prepared by coupling agent N-succinimidyl-3-(2-pyridyl-dithio)-propionate (SPDP,

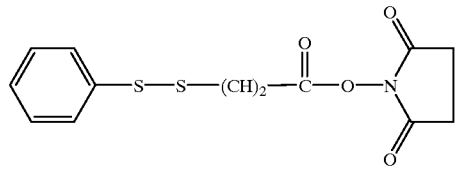

The steps of synthesis were shown as following:
4.1.1. Preparation of LOP-PDP (Ligand oligopeptide 3-(2-pyridyldithio)-propionate):

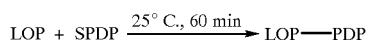

The molar ratio of LOP to SPDP is 1:8.
The different type of LOP was dissolved in different buffer and SPDP in anhydrous ethanol. The reaction product LOP-PDP was obtained after dialysis to remove the unreacted SPDP.
4.1.2. Preparation of PCP-$(SH)_2$(polycationic polypeptide-$(SH)_2$)

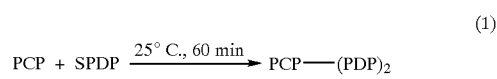

(1)

The molar ratio of PCP to SPDP was 1:2

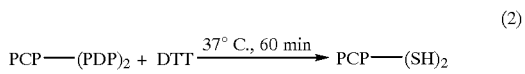  (2)

PCP-(PDP)$_2$: polycationic polypeptide (3-(2-pyridyldithio))-propionate)$_2$

The different type of PCP (polylysine, protamine or histone) was dissolved in different type of buffer. The reaction product was dialyzed against the relevant buffer system to obtain the intermediate product PCP (PDP)$_2$ and product PCP-(SH)$_2$. The final concentration of Dithiothreitol (DTT) in reaction (2) was 25 mM.

4.1.3. Preparation of (LOP)$_2$-PCP

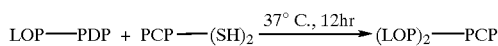

The molar ratio of LOP-PDP to PCP-(SH)$_2$ were 10:1. The reaction was carried out in the relevant buffer system. After Sephadex G50 chromatography of the reaction mixture, PCP-(LOP)$_2$ was collected in the first peak of eluate. The amino acid composition analysis was performed to confirm that the collected material was the final product as expected.

4.2. Preparation of (EROP)$_2$-PCP

The similar method was used to prepare EROP-PCP by utilizing SPDP as coupling reagent.

4.2.1. Preparation of EROP-PDP endosome-releasing oligopeptide 3-(2-pyridyldithio)-propionate)

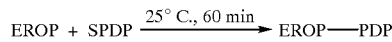

The molar ratio of EROP to SPDP was 1:10. The reaction was carried out in the relevant buffer system. The product EROP-PDP was obtained after dialysis against the buffer.

4.2.2. Preparation of PCP-(SH)$_2$

The method was same as 4.1.2

4.2.3. Preparation of (EROP)$_2$-PCP

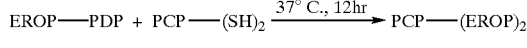

The molar ratio of EROP-PDP to PCP-(SH)$_2$ was 10:1. The reaction was carried out in the relevant buffer system. After Sephadex G50 chromatography of the reaction mixture, PCP-(EROP)$_2$ was collected in the first peak of eluate. The amino acid composition analysis was performed to confirm that the collected material was the final product as expected.

4.3. Preparation of (LOP)$_2$-PCP-(EROP)$_2$
4.3.1. Preparation of (LOP)$_2$-PCP The method was same as 4.1

4.3.2. Preparation of (LOP)$_2$-PCP-(PDP)$_2$

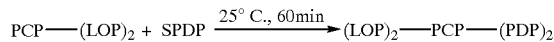

The molar ratio of PCP-(LOP)$_2$ to SPDP was 1:2. The reaction was performed in the relevant buffer system. After the reaction has been completed, the reaction product (LOP)$_2$-PCP-(PDP)$_2$ was recovered by dialysis against the buffer to remove the small molecular weight reagents.

4.3.3. Preparation of EROP-SH (Endosome release oligopeptide-SH)

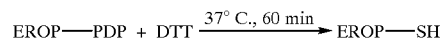

EROP-PDP was prepared according to the method in 4.2.1. The reaction was performed in the relevant buffer system. After dialysis of the reaction mixture, the product EROP-SH was collected. The final concentration of DTT in reaction was 25 mM.

4.3.4. Preparation of (LOP)$_2$-PCP-(EROP)$_2$

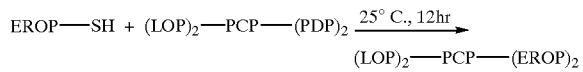

The molar ratio of EROP-SH to (LOP)$_2$-PCP-(PDP)$_2$ was 10:1. The reaction was performed in the relevant buffer system. The final product (LOP)$_2$-PCP-(EROP)$_2$ was collected from the first peak by Sephadex G50 chromatography. The product identity was confirmed by amino acid composition analysis.

5. Example 5

Isolation and Purification of DNA

Recombinant plasmid DNA for eukaryotic cell expression used in the present invention was isolated and purified by using Niaxi plasmid Kit provided by QIAGEN according to its protocols.

Single bacterial colony was inoculated into 5 ml LB medium containing antibiotics, incubated at 37° C. with shaking at 220 rpm overnight, then transferred to 200 ml LB with antibiotics and shaked at 37° C. overnight. 200 ml culture was centrifuged in 500 ml bottle at 2,500 rpm, 4° C. for 5 min. The precipitate was dried and thoroughly dispersed and suspended in 10 ml P1 buffer(Tris.HCl pH 8.0 50 mM, EDTA 10 mM, RNase A 100 $\mu$g/ml) by blowing with pipette. The suspension was transferred to 50 ml plastic tube. 10 ml P2 buffer (200 mM NaOH, 1%SDS) were added, mixed by inverting for 4–6 times and kept at room temperature for 5 min. Then 10 ml buffer P3 (3.0 M NaAc, pH 5.5) were added. Mixed immediately by inverting for 5–6 times, kept in ice bath for 20 min, and centrifuged at 4° C., 12,000 rpm for 20 min. After filtration, the supernatant was loaded onto QIAGEN Tip 500 previously equilibrated with 10 ml QBT buffer. The Tip was washed twice with 30 ml QC buffer, then eluted with 15 ml QF buffer. DNA was isolated by addition of 0.7 volume of isopropanol kept at room temperature, immediately centrifuged at 4° C., 12,000 rpm for 30 min. The precipitate was washed with 5 ml 70% ethanol and air dried for 5 min. DNA was dissolved in an appropriate amount of TE. The purity was checked by UV spectrophotometry and quantitated.

6. Example 6

Preparation of Polypeptide/DNA Complex 6.1. Preparation of LOP-PCP/EROP-PCP and DNA complex(Complex of DNA with (LOP)$_2$-PCP and (EROP)$_2$-PCP)

(LOP)$_2$-PCP and (EROP)$_2$-PCP were mixed in a molar ratio of 1:1 in normal saline and sterile-filtrated. DNA dissolved in normal saline was also sterile-filtrated. DNA was dropwise added to the (LOP)$_2$-PCP and (EROP)$_2$-PCP mixture with constant stirring according to w/w ratio of DNA/polypeptide at 1.5:1. The mixture was kept at 25° C. for 0.5 hr.

The complex was monitored by agarose gel (1%) electrophoresis. The 100–150 nm particles of DNA/polypeptide were identified by electron microscope examination.

6.2. Preparation of 4-element complex (LOP)$_2$-PCP-(EROP)$_2$/DNA (LOP)$_2$-PCP-(EROP)$_2$ was dissolved in normal saline and sterile-filtrated. Sterile DNA solution in normal saline was added drop-wise to the polypeptide solution by constant stirring according to w/w ratio of DNA to polypeptide at 1.5:1. The reaction mixture was incubated at 25° C. for 0.5 hr. the agarose gel (1%) electrophoresis was performed to examine the complex formation. The particle size of polypeptide/DNA complex was examined by electron microscope.

7. Example 7

In vitro Gene Transduction

Cells($5 \times 10^4$) were seeded into 6-well plate(Costar) and incubated. 1 day later, cells were incubated in fresh medium of DMEM containing 10% (v/v) calf serum. 2 days later, the complex of DNA of LOP/PCP and EROP-PCP (containing 0.2 μg DNA) was added. After 12 hr incubation, the medium containing DNA polypeptide complex was replaced with fresh medium. The efficiency of gene transfer was examined by using the complex of pSV-β-galactosidase with LOP/PCP and EROP-PCP polypeptide for in vitro transduction. The β-galactosidase activity of cells was examined at 24,48,72, 96,120,144 and 168 hr respectively after the addition of DNA/polypeptide complex.

β-galactosidase cytochemistry examination was performed as following: cells were washed with PBS after removal of medium, fixed with 4% formaldehyde at 4° C. for 5 min and washed with PBS. Cells were stained with X-gal solution containing X-gal 1 mg/ml, $K_4$[Fe(CN)6] 5 mM, $K_3$[Fe(CN)$_6$] 5 mM and $MgCl_2$ 2 mM at 37° C. for 24 hr.

8. Example 8

In vivo Gene Transduction

The in vivo gene transfer was to inject the present 4-element polypeptide/DNA complex described in Example 6 around tumor transplanted subcutaneously in nude mice or SCID mice. The procedures are as following:

8.1. Preparation of DNA/polypeptide complex described in Example 6

8.2. In vivo gene transfer into tumor

The DNA/polypeptide complex was injected around the tumor transplanted subcutaneously in nude mice or SCID mice. The dose of the complex was equivalent to 0.2 kg DNA per mouse. At different time intervals after injection, the tumor was dissected after sacrifice of animals. Half of the tumor of each animal was used for pathology and cytochemical examination and the other half for direct staining with X-gal solution (Same as procedures in Example 5). For whole tumor tissue examination, the tissue was briefly washed with PBS, fixed in 4% formaldehyde at 4° C. for 15 min, followed by washes with PBS 10 min for 3 times. The tissue was stained with X-gal solution at 37° C. for 24 hr. (same as procedures in Example 7). For pathology and cytochemistry examination, the tissues was fixed in 4% formaldehyde and then stained by X-gal using protocols as above. After frozen sectioned, the tissue was further stained by Fast Nuclear red or hemotoxylene-eosin.

To examine the in vivo targetability of the complex gene transfer system, corresponding conrol was used.

8.3. To examine the therapeutic effect for treatment of cancer, genes related to cell apoptosis were introduced by the present targeting gene transfer system. The polypeptide/DNA complex was administrated by injection around tumor or through blood vessels. The dose was dependent on different condition of experiments. The therapeutic efficacy of genes related to apoptosis or other functions was shown in Examples described below.

9. Example 9

E5 4-element Complex Gene Transfer System Targeted to Cells that Expressed IGF-I Receptor or IGF-II Receptor 9.1. Composition of E5 gene transfer system.

LOP: amino acid sequence of oligopeptide E5, EPFRS POLAL ETGY, (SEQ ID NO.1).

PCP: molecular weight of polylysine 26,000.

EROP: amino acid sequence of HA20, GLFEA IAEFI EGGWE ELIEG, (SEQ ID NO.5).

DNA: β-gal gene, CKI genes p21$^{WAF-1}$, P15, P16.

9.2. Preparation E5-PCP and HA20-PCP was according to Example 4. The buffer system used for E5 was 0.1 M PBS/0.1 M NaCl at pH 7.5, for HA20 0.1 M PBS/0.1 M NaCl at pH 7.8.

9.3. Preparation of DNA/polypeptide complex using E5-polylysine and HA20-polylysine was according to methods in Example 6. The optimal ratio of DNA to polypeptide was 1.5:1 (w/w), equivalent to molar ratio of 1:75–80.

9.4. In vitro gene transfer of β-galactosidase gene(pSV β-gal) into human hepatoma cell line SMMC-7721 and hepatocyte line L02.

Methods of gene transfer were similar to Example 7. Results were shown in Table 1–3 and FIGS. 9–12. From table 1, it was demonstrated that only the E5-polylysine and HA20-polylysine used together would be able to transduce pSV β-gal DNA into human hepatoma SMMC-7721 cells at an efficiency of 60%, while the E5-polylysine/DNA complex is at low efficiency (<10%) possibly due to lysozyme degradation. Moreover, the HA20-polylysine itself had very low efficiency to transduce the β-gal gene DNA into hepatoma cells.

Table 2 illustrated that E5 4-element complex could transfer β-gal gene into SMMC-7721 hepatoma cells, but not to the normal hepatocyte L02 or primary culture hepatocytes R02. Table 3 indicated that expression of β-gal gene started at 48 hr after transfection and reached its peak at 72 hr.

FIGS. 9–12 demonstrate the E5 gene transfer system can efficiently target β-gal gene to human hepatoma cell SMMC-7721, but not to normal hepatocyte L02 and primary culture hepatocytes R02. Cells were stained with X-gal at 72 hr after transfection.

Figure 32:
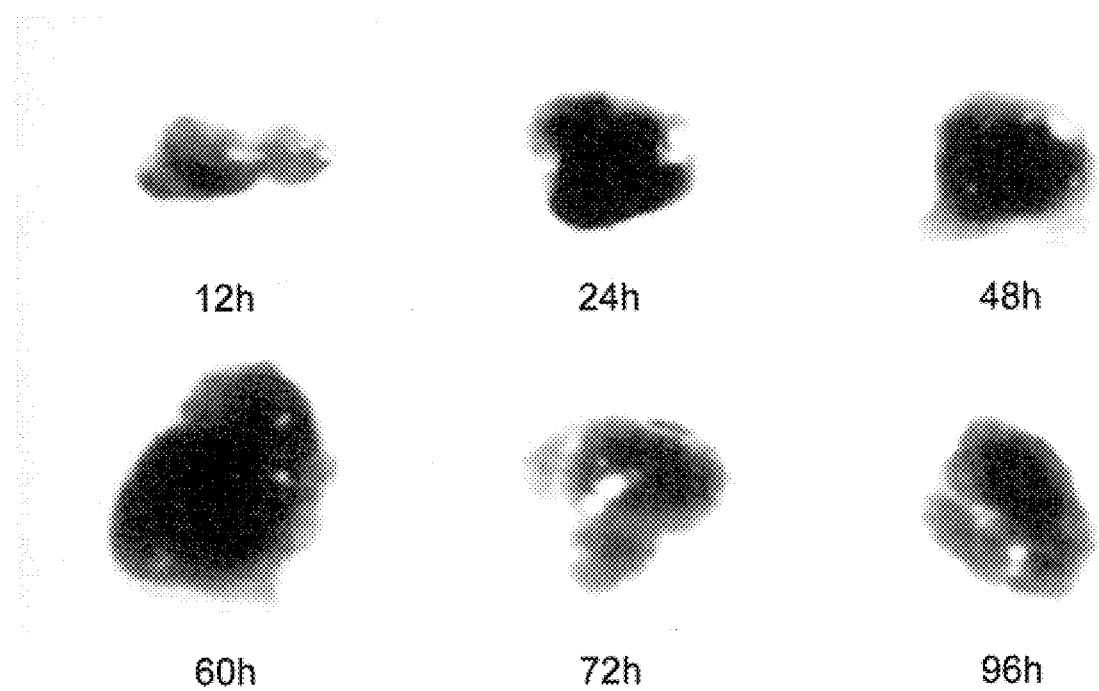
FIG. 32. The in vivo transduction of β-gal gene mediated by E5 4 element system into tumor of SMMC-7721 hepatoma subcutaneously transplanted in nude mice. The DNA/polypeptide complex was administrated subcutaneously surrounding the tumor mass. Tumor was dissected at different time intervals as indicated and stained with X-gal.
Figure 33:
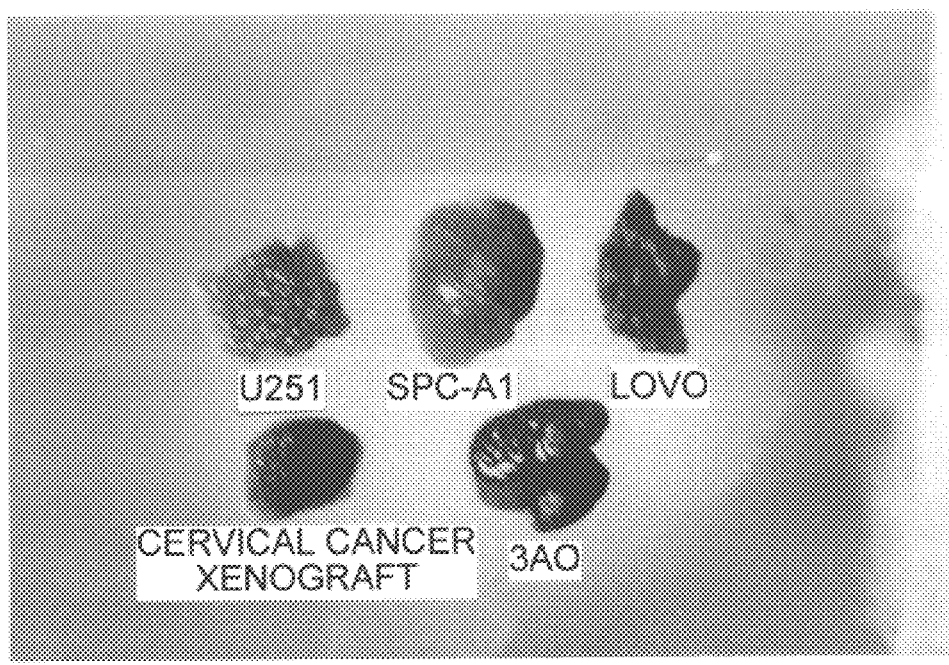
FIG. 33. Results of in vivo transduction of β-gal gene mediated by GE7 4 element system by injection of DNA/polypeptide cernplex surrounding the tumor mass of human cancer subcutaneously transplanted in nude mice. Tumor nodules were dissected and stained with X-gal. SMMC-7721 was human hepatoma; BEL-7402, human hepatoma; SPC-A1, human lung adenocarcinoma; 3A0, human ovarian cancer; LOVO, human colon adenocarcinoma; SGC, human gastric cancer; Bcap-37, human mammary cancer; U251, human glioblastoma; H128, human lung small cell carcinoma. The cervical cancer was a xenograft in nude mice. The positive results were observed in all the cancer types except H128. The administration of DNA/polypeptide complex and X-gal treatment were same as shown in previous Figures.
Figure 33:
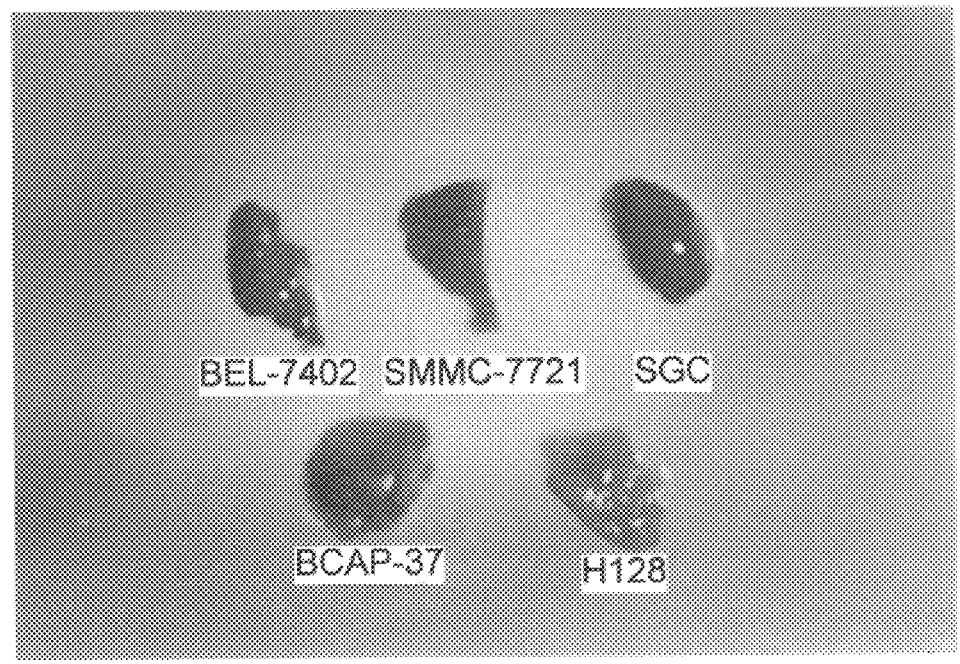
Figure 34:
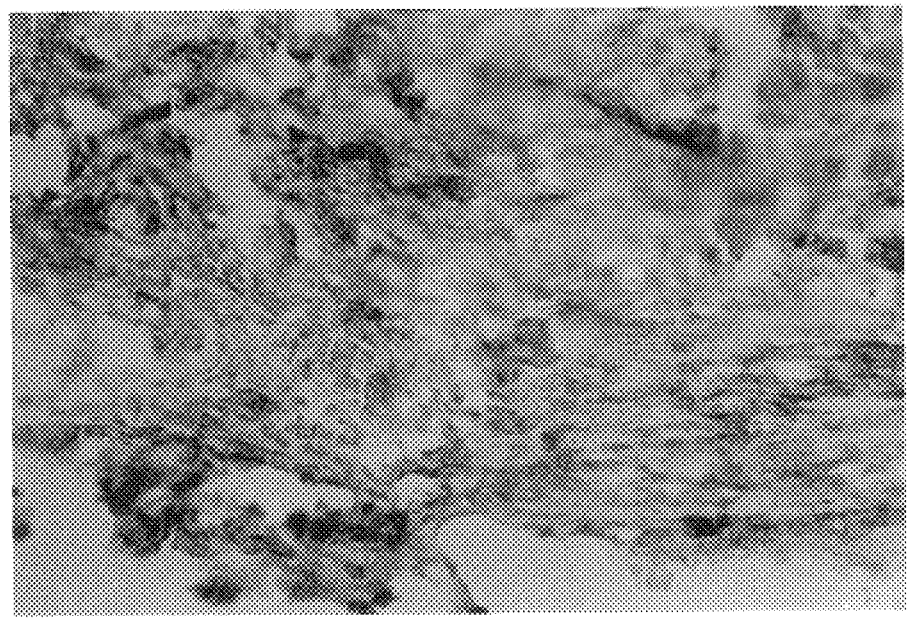
FIG. 34. The pathological examination of human hepatoma SMMC-7721 transplanted in nude mice after in vivo transduction with β-gal gene in GE7 4 element system. The section was stained with X-gal. Positive results were observed.
Figure 35:
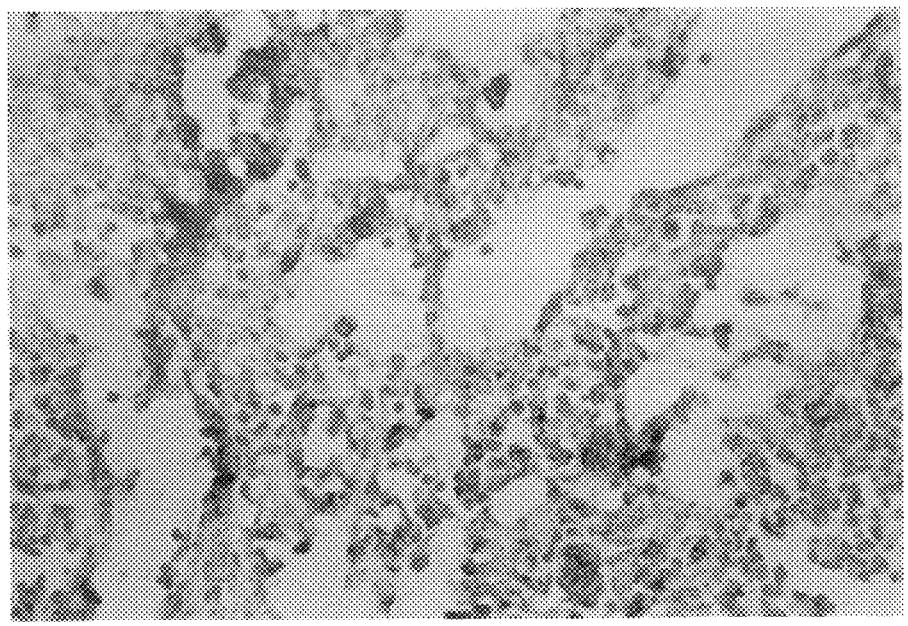
FIG. 35. The pathological examination of human hepatoma BEL-7402 transplanted in nude mice after in vivo transdution with β-gal gene in GE7 4 element system. The methods were same as FIGS. 33, 34. Positive results were observed.
Figure 36:
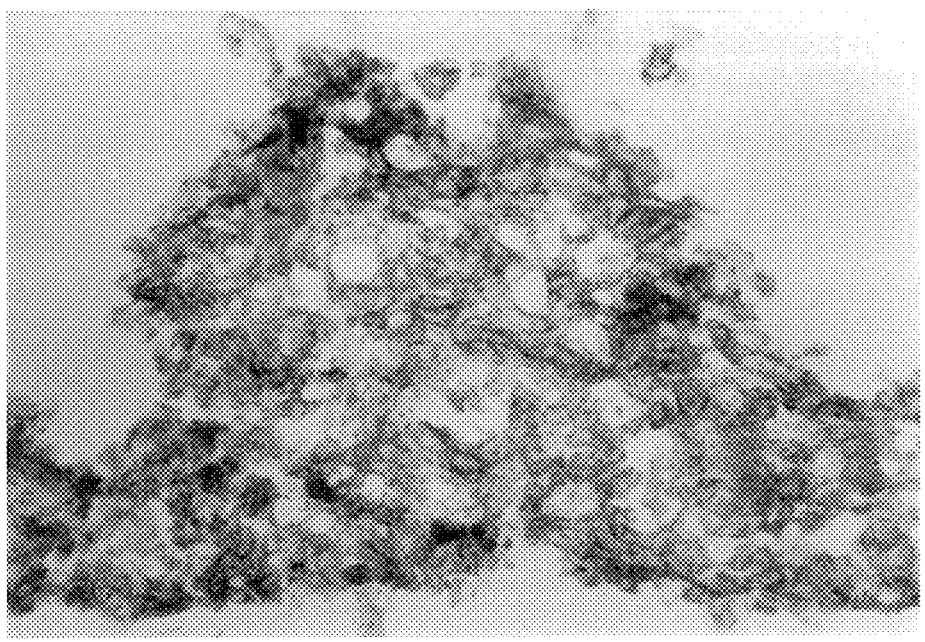
FIG. 36. The pathological and X-gal cytochemistry examination of human glioma U251 transplanted in nude mice after in vivo transduction with β-gal gene in GE7 4 element complex.
Figure 37:
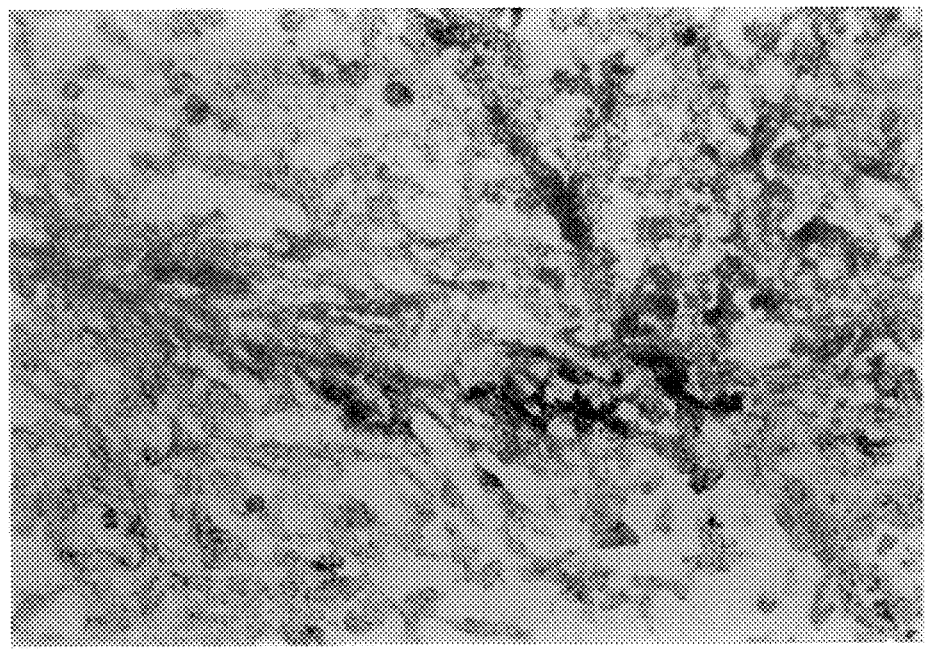
FIG. 37. The pathological and X-gal cytochemistry of human ovarian cancer 3A0 transplanted in nude mice. The β-gal gene was transduced in vivo by GE7 4 element system as indicated in FIGS. 34–36. Positive results were observed.
Figure 38:
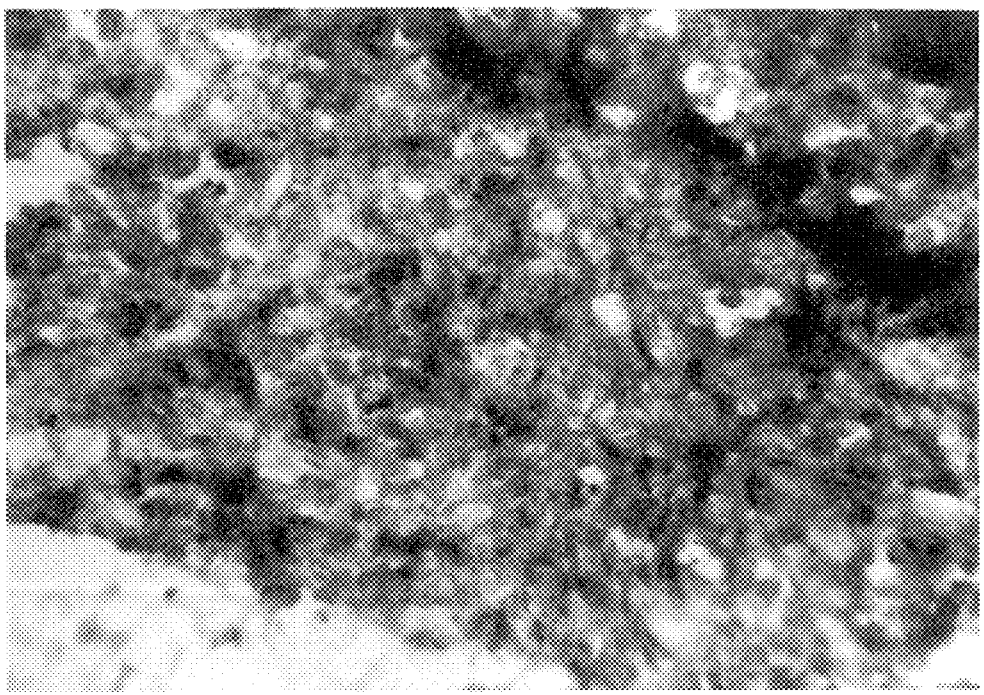
FIG. 38. The pathological and X-gal cytochemistry examination of human lung adenocarcinoma SPC-A1 transplanted in nude mice. The β-gal gene was transduced in vivo by GE7 4 element system. Positive results were observed.
Figure 39:
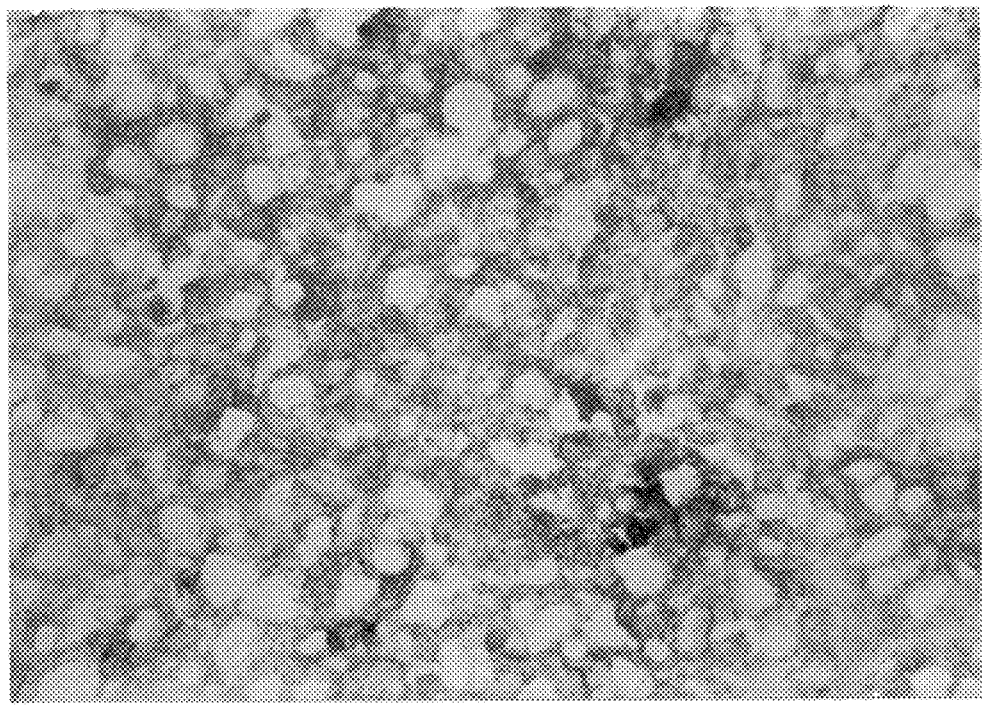
FIG. 39. The pathological and X-gal cytochemistry examination of human colon cancer LOVO transplanted in nude mice. The β-gal gene was transduced in vivo by GE7 4 element system. Positive results were observed.
Figure 40:
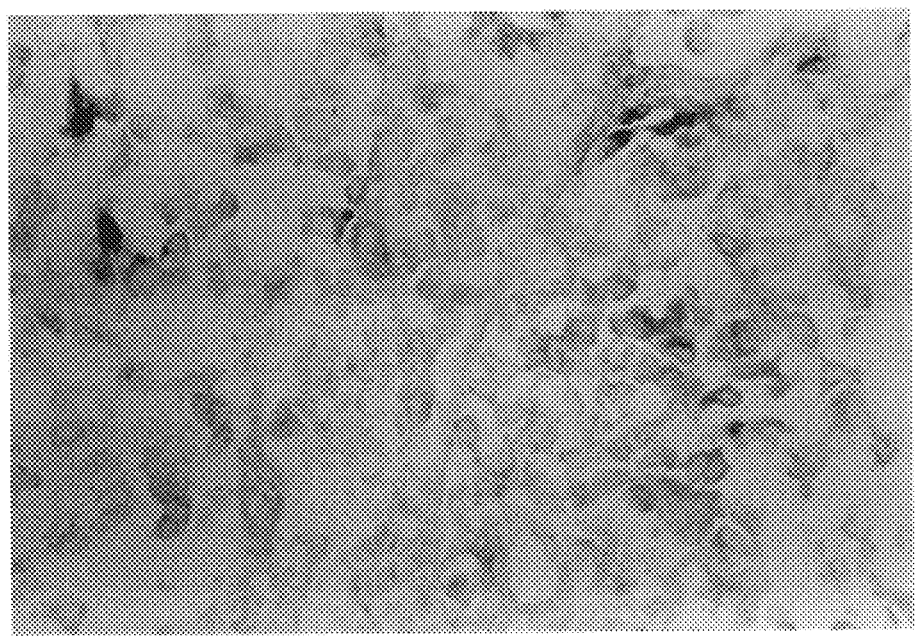
FIG. 40. The pathological and X-gal cytochemistry examination of human gastric cancer SGC transplanted in nude mice. The β-gal gene was transduced in vivo by GE7 4 element system. Positive results were observed.
Figure 41:
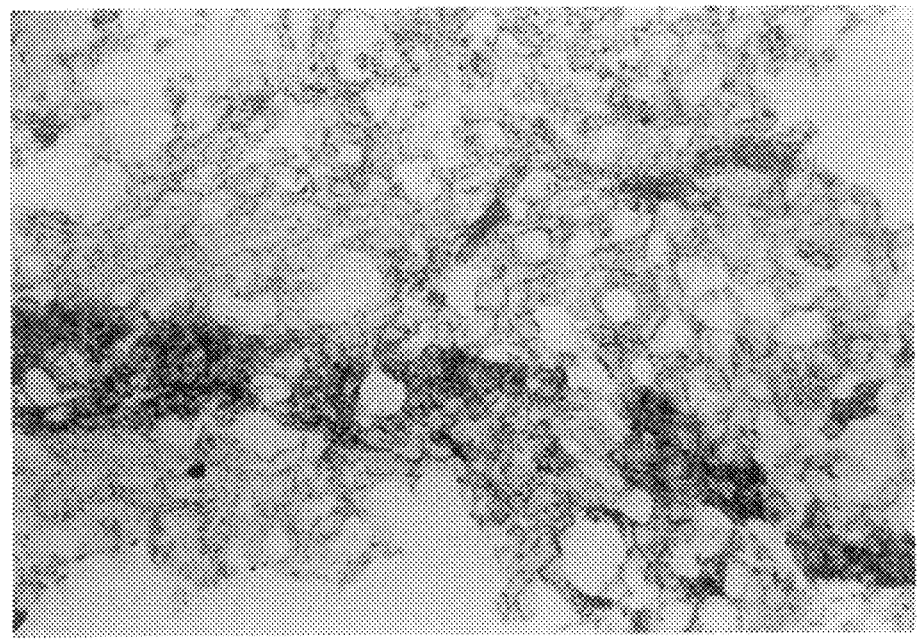
FIG. 41. The pathological and X-gal cytochemistry examination of a xenograft of human cervical cancer in nude mice. The β-gal gene was transduced in vivo by GE7 4. Positive results were observed.
Figure 42:
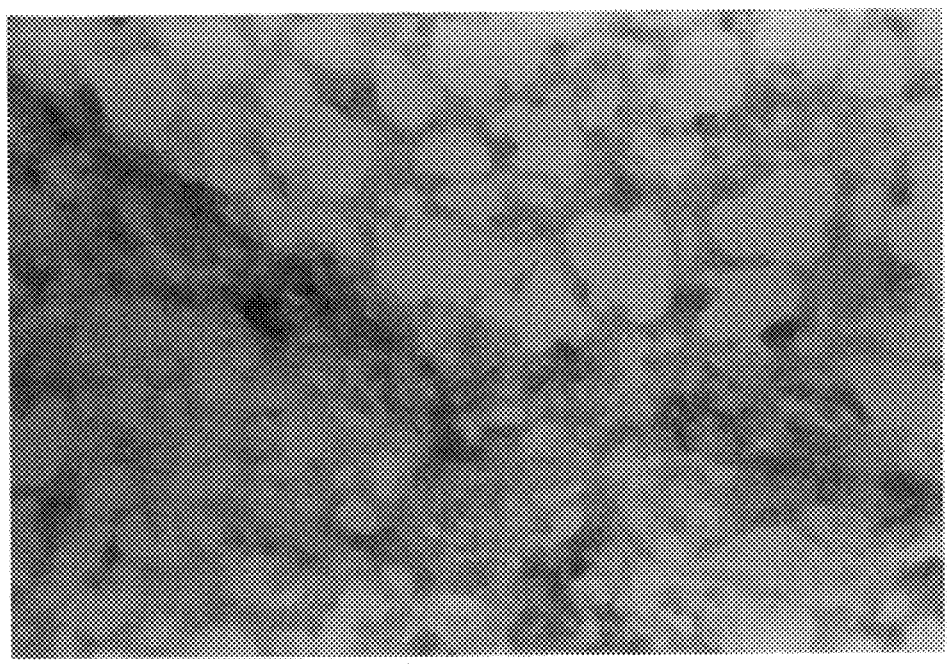
FIG. 42. The pathological and X-gal cytochemistry examination of human lung small cell carcinoma H1128 transplanted in nude mice transduced in vivo with β-gal mediated by GE7 4 element system. Negative results were observed, indicating that GE7 4 element failed to transfer gene into cancer cell without EGF receptor expression.

9.5. In vivo gene transfer of pSV β-gal DNA into human hepatoma 7721 in nude mice mediated by 100 μl E5 4-element complex (E5-polylysine/HA20-polylysine/pSV-β-gal DNA) containing 20 μg β-gal DNA was injected subcutaneously around the tumor. The expression of transduced β-gal gene was observed at 12 hr after transduction and persisted till 96 hr. The expression was only observed in β-gal DNA complex with E5-polylysine and HA20 polylysine and barely detected by β-gal DNA itself(FIG. 32).

9.6. In vitro transduction of CKI genes into human hepatoma cell lines using E5-polylysine/HA20-polylysine system—the inhibitory effect on cancer cell growth and induction of apoptosis.

E5-polylysine/HA20-polylysine was used to transduce CKI genes (p21$^{WAF-1}$, p15 and p16) in vitro into human hepatoma cells SMMC-7721. The inhibitory effect on tumor cell growth was shown in FIG. 30.

Figure 30:
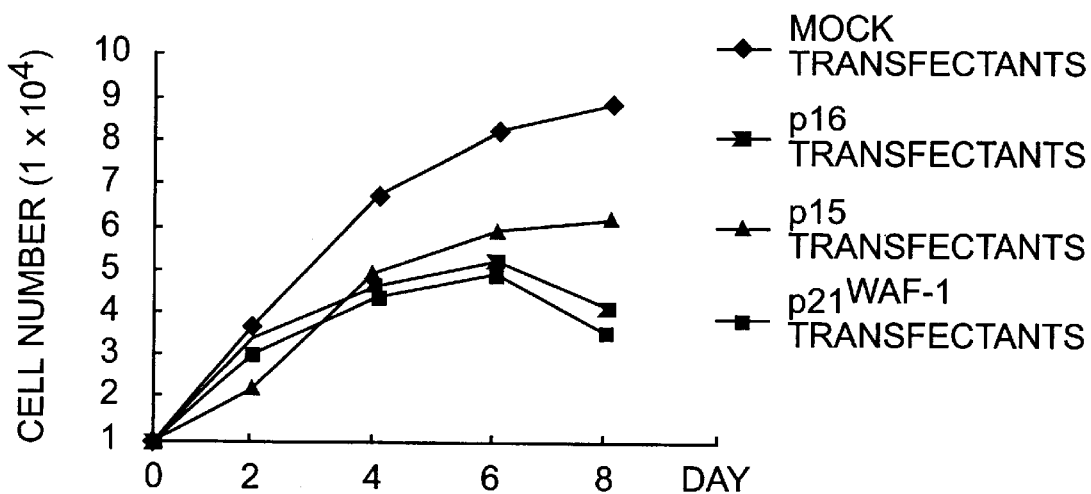
FIG. 30. The growth curve of SMMC-7721 human hepatoma cells after transduction with p15, p16 and $p21^{WAF-1}$ cDNA mediated by E5 4 element system. The ● indicated polypeptide vector, ■, p15; ▲, p16; ◆, $p21^{WAF-}$.
Figure 31:
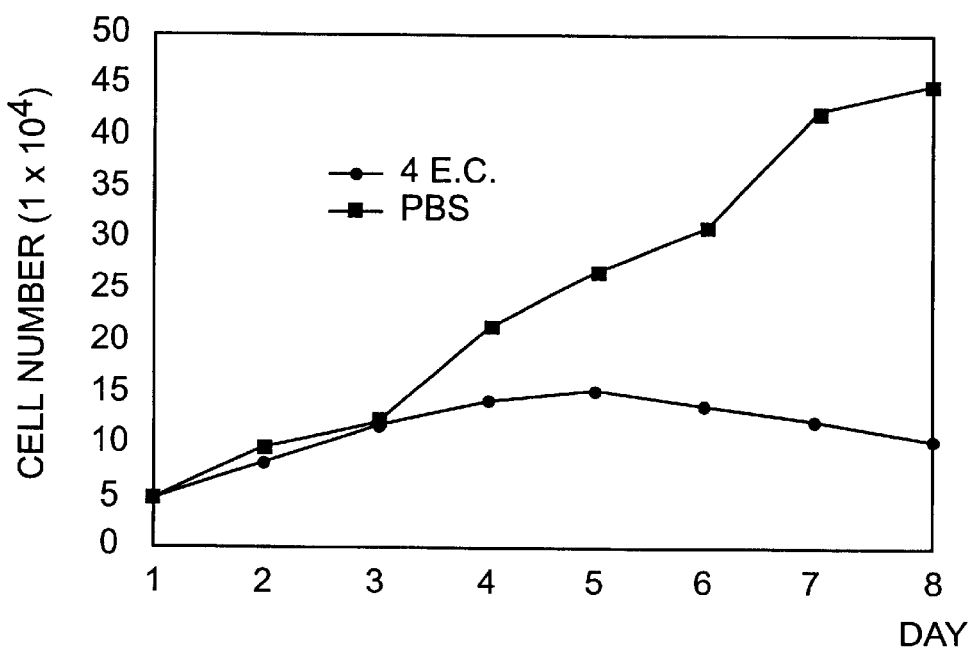
FIG. 31. The growth curve of BEL-7402 human hepatoma cells after transduction with $p21^{WAF-1}$ cDNA mediated by GE7 4 element system. The symbol ■ denoted the PBS control; ◆, $p21^{WAF-1}$ transduced.

$1-2 \times 10^5$ human hepatoma SMMC-7721 cell were cultured with E5-polylysine/HA20-polylysine/CKI DNA containing 0.2 μg DNA per ml and with composite polypeptide vector containing no DNA as control. 24 hr after transfection, culture was replaced with fresh medium and incubated for 48 hr. Cells were then trypsinized. $1 \times 10^4$ cells/well were seeded into 24 well plates. Cells were counted every 48 hr for 4 times. The growth curve of cells was made based on the average value of cell counts from each 3 wells(FIG. 30).

Figure 45:
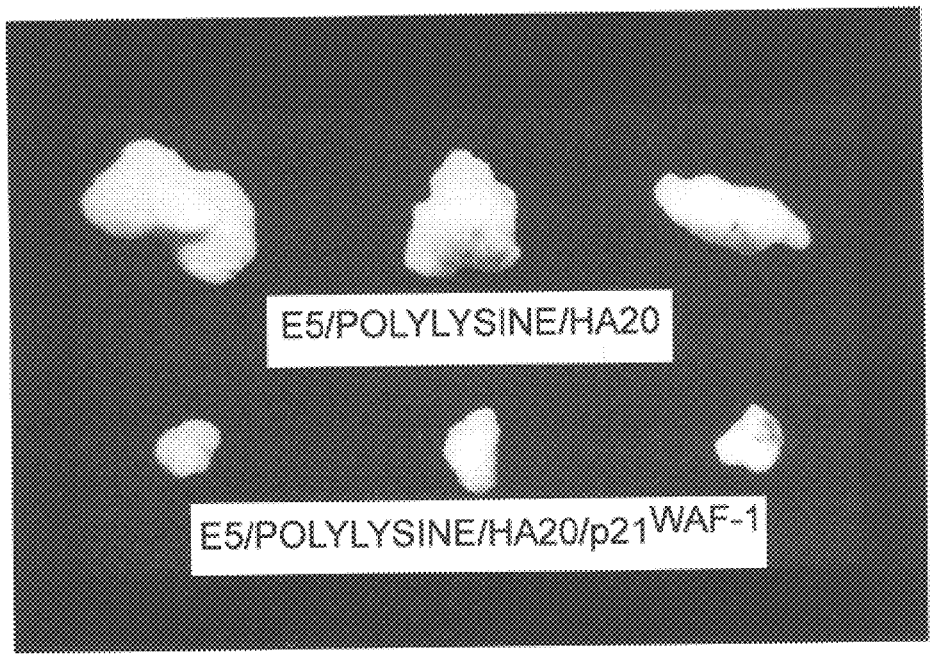
FIG. 45. Inhibitory effect of $p21^{WAF-1}$ cDNA on the growth of human hepatoma SMMC-7721 in nude mice by in vivo transduction mediated by E5 4 element system (E5/polylysine/HA20/$p21^{WAF-1}$ cDNA). The polypeptide vector (E5/polylysine/HA20) itself was used as control.

9.7. Inhibitory effect of p21$^{WAF-1}$ gene transduced in vivo mediated by E5-polylysine and HA20-polylysine/p21$^{WAF-1}$ system on human hepatoma in nude mice.

p21$^{WAF-1}$ gene was transduced in vivo by direct injection of 100 μl complex of E5 polylysine/HA20/polylysine and DNA around human SMMC-7721 hepatoma transplanted subcutaneously in nude mice. The doses of polypeptide and DNA were 20 kg, twice a week, for two weeks. 17 days after injection, tumors were dissected after sacrifice of animals. The inhibitory effect was demonstrated in Table 7 and FIG. 45.

10. Example 10

GE7 4-element Gene Transfer System to Target Exogenous Genes into Cells Enriched of EGF Receptor or C-erb B Family Members.

10.1. Composition of GE7 gene transfer system

LOP: amino acid sequence of oligopeptide GE7 NPVVG YIGER PQYRD L, (SEQ ID NO.2)

PCP: polylysine, molecular weight 26,000; protamine, molecular weight 8,000 (pharmaceutical use).

EROP: HA20 same as Example 9.

DNA: β-gal gene, p21$^{WAF-1}$ gene.

10.2. Preparation of GE7-PCP and HA20-PCP

Preparation of GE7-PCP and HA20-PCP was according to methods in Example 4. The buffer system used for GE7 was 0.1 M PBS/0.1 M NaCl at pH 7.4, for HA20 0.1 M PBS/0.1 M NaCl at pH 7.8.

10.3. Preparation of DNA/polypeptide complex using GE7-polylysine and HA20-polylysine, or GE7-protamine and HA20-protamine.

The general procedures were same as methods in Example 6.1. The optimal ratio of DNA to polypeptide was 1.5:1 for polylysine system (w/w), 1:1(w/w) for protamine system equivalent molar ratio of 1:75–80.

10.4. In vitro transfer of β-galactosidase gene, pSV-β-gal DNA into human hepatoma cell line SMMC-7721, BEL-7402, glioma cell line U87, ovarian cancer cell line 3A0,A0, breast cancer cell line Bcap-37, lung adenocarcinoma line SPC-A1 and hepatocyte line L02, mouse fibroblast cell line NIH/3T3.

Methods of gene transfer were according to procedures in Example 7. Results were shown in Table 4–6 and FIGS. 13,15–26. From Table 4, it was demonstrated that only the GE7-polylysine and HA20-polylysine, GE7-protamine and HA20-protamine would be able to transduce pSV-β-gal DNA into human hepatoma SMMC-7721, BEL-7402 cells at an efficiency of 80%, 90% respectively; 65% for ovarian cancer cell line 3A0; 15% for ovarian cancer cell line A0; 80% for lung cancer cell line SPC-A1; 30% for glioma cell line U87 and 80% for breast cancer cell line Bcap-37. The GE7-polylysine/DNA complex, GE7-protamine/DNA complex without HA20 had low efficiency of transduction (<10%) possibly due to the lysosomal enzyme degradation. Moreover, HA20-polylysine/β-gal, HA20-protamine/β-gal, polylysine/β-gal and β-gal DNA alone had very low efficiency (<0.1%) in transducing the β-gal DNA into above cancer cell lines.

It was illustrated in Table 5, the GE7 4-element complex system had extremely low efficiency (<0.1%) in transducing β-gal gene into normal hepatocyte L02 and mouse NIH/3T3 fibroblast. Table 6 indicated the time course of β-gal gene transduced in BEL-7402 cells. The expression initiated at 24 hr after transfection and reached the peak at 168 hr.

10.5. In vivo gene transduction of β-gal gene mediated by GE7 4-element complex system into human malignant tumors subcutaneously transplanted in nude mice.

Human malignant tumor, hepatoma BEL-7402, SMMC-7721, glioblastoma U251, breast cancer Bcap-37, ovarian cancer 3A0, lung adenocarcinoma SPC-A1, lung small cell carcinoma H128, gastric cancer SGC, colon cancer LOVO and cervical cancer xenograft were subcutaneously transplanted in nude mice. 100 μl of GE7 4-element complex containing 0.2 μg β-gal plasmid DNA was injected subcutaneously surrounding the tumor. FIGS. 34–41 illustrated that GE7 4-element complex can transfer β-gal gene with high efficiency and targetability into transplanted BEL-740; SMMC-7721, U251, Bcap-37, 3A0, SPC-A1, SGC, LOVO and cervical cancer. However, no β-gal transfer could be observed in EGF R (–) human lung small cell carcinoma H128.

Expression of transduced β-gal gene was examined at 4, 8, 12, 24, 48, 96 hr, 7, 15, 20, 30 and 40 day after transfection in vivo. β-gal gene expression initiated at 4 hr, reached its peak at 24 to 48 hr and persisted till 40 days. Only the 4-element complex of GE7-polylysine/HA20-polylysine/β-gal or GE7-protamine/HA20-protamine/β-gal complex could transfer β-gal gene into tumor cells in vivo with high efficiency, while GE7-polylysine/β-gal, HA20-polylysine/β-gal, polylysine/β-gal and β-gal DNA itself could almost not transduce β-gal gene into tumor cells.

10.6. In vivo inhibitory effect of CKI gene p21$^{WAF-1}$ on growth of human hepatoma subcutaneously transplanted in nude mice.

Figure 46:
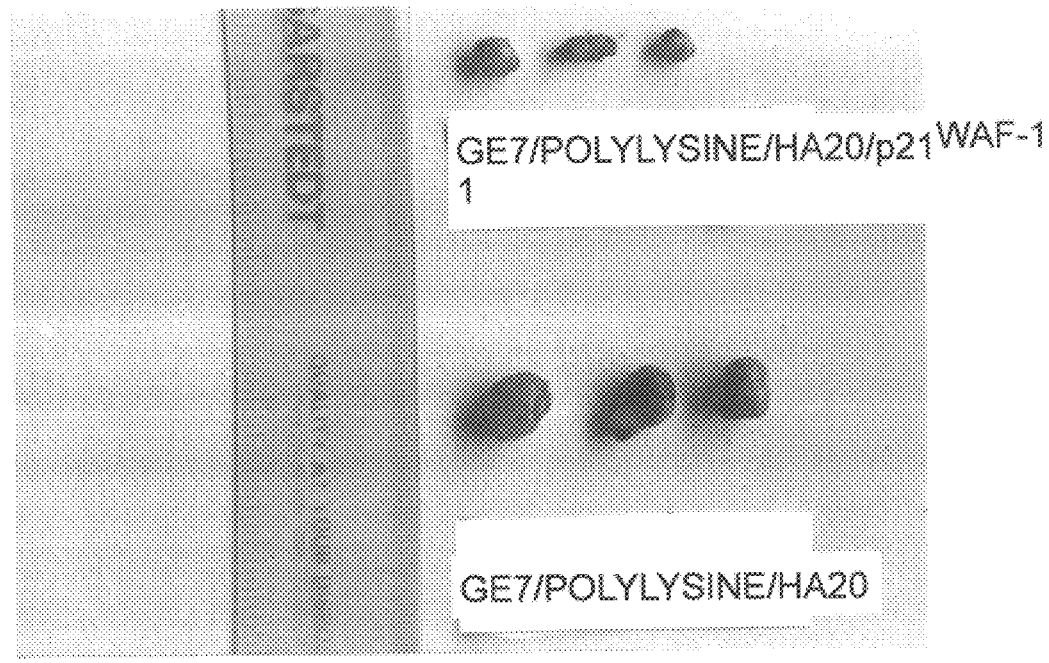
FIG. 46. Inhibitory effects of $p21^{WAF-1}$ cDNA on the growth of human hepatoma BEL-7402 transplanted in nude mice by in vivo transduction with $p21^{WAF-1}$ cDNA mediated by GE7 4 element complex (GE7/Polylysine/HA20/$p21^{WAF-1}$ cDNA). The polypeptide vector itself (GE7/Polylysine/HA20) was transduced as control.

GE7-polylysine/HA20-polylysine/p21$^{WAF-1}$ DNA 4-element complex was injected into hepatoma subcutaneously transplanted in nude mice. Normal saline, p21$^{WAF-1}$ plasmid DNA, GE7-polylysine/HA20-polylysine without p21$^{WAF-1}$ were injected around tumor as controls. Each group had 6 animals. The dose of p21$^{WAF-1}$ DNA was 0.2 μg and that of polypeptide was 0.13 μg per mouse. Animals were sacrificed at 14 day after treatment. Weight and volume of tumor were measured. The inhibitory rate was calculated and illustrated in Table 8 and 9. The inhibitory effect of p21$^{WAF-1}$ on tumor growth was demonstrated in FIG. 46.

11. Example 11

The targeting gene transfer mediated by GV1 and GV2 4-element complex system.

11.1. Composition of GV1 and GV2 4-element complex gene transfer system

LOP: amino acid sequence of GV1: CHPIE TLVDI EQEYP DEIEY IFKPS PVPLM RP, (SEQ ID NO.3); amino acid sequence of GV2: PVPTE ESNIT MQIMR IKPHQ GQHIG EMSFL QHNKC E, (SEQ ID NO.4).

PCP: protamine, MW~7,000,

EROP: amino acid sequence of HA20 is same as Example 9.1,

DNA: β-gal(pSV-β-gal) plasmid.

11.2. Preparation of GV1-protamine, GV2-protamine and HA20-protamine polypeptide The oligopeptide GV1 or GV2, and HA20 were covalently coupled with protamine by SPDP as shown in Example 4.

11.2.1. Preparation of Protamine-PDP

Protamine and SPDP were mixed according to a molar ratio of 1:5, diluted with 0.1 M NaCl-0.1 M phosphate buffer at pH 7.4, to a concentration of protamine at 1 mg/ml. Reaction was performed at 25° C. for 2 hr. The product protamine-PDP was purified with Sephadex G-25 column chromatography(50 cm×3 cm) by elution with the above buffer so as to remove the residual SPDP.

11.2.2. Preparation of GV1-protamine and GV2-protamine

GV1 or GV2 was mixed with protamine-PDP at a molar ratio of 1:1. The reaction was carried out at 25° C. for 24 hr.

GV1-protamine or GV2-protamine was purified with Sephadex G-50 column chromatography (70 cm×1.8 cm) by elution with H₂O. The product was concentrated and quantitated by UV spectrophotometry.

11.2.3. Preparation of protamine-(SH)₂

Protamine-PDP was reacted with excess amount of DTT (2 mM) at 25° C. for 40 min to produce protamine-(SH)₂. The product was purified with Sephadex G-25 column chromatography (50 cm×3 cm) to remove residual DTT by elution with 0.1 M NaCl-0.1 M phosphate buffer, pH 7.4.

11.2.4. Preparation of HA20-PDP

HA20 was mixed with SPDP at a molar ratio of 1:5 and reacted at 25° C. for 2 hr. The product HA20-PDP was purified as described in 11.2.1.

11.2.5. Preparation of HA20-protamine

HA20-PDP was mixed with protamine-(SH)₂ at a molar ratio of 1:1. Reaction was performed at 25° C. for 72 hr. The product HA20-protamine was purified with methods as 11.2.2.

11.3. Preparation of 4-element complex of GV1-protamine/HA20-protamine/β-gal and GV2-protamine/HA20-protamine/β-gal gene transfer system 11.3.1. Preparation of β-gal plasmid DNA Same as described in Example 5.

Figure 8:
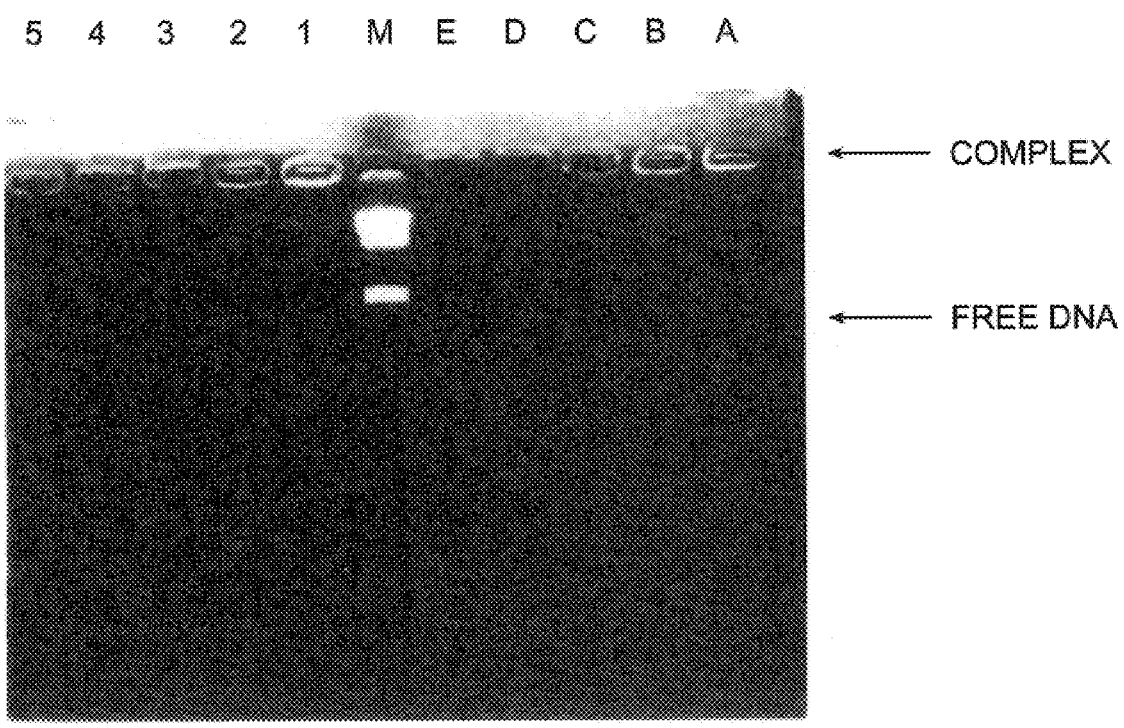
FIG. 8. Gel retardation analysis of the $GV_1$ and $GV_2$ 4 element complex by 1% agarose gel electrophoresis. 1,2,3, 4,5 denote $GV_1$ complex containing a W/W ratio of DNA to polypeptide at 1:2, 1:3, 1:4, 1:5, 1:6; A, B, C, D, E denote $GV_2$ complex containing a W/W ratio of DNA to polypeptide at 1:2, 1:3, 1:4, 1:5, 1:6 respectively. M is the λ DNA Hind III digest marker.
Figure 9:
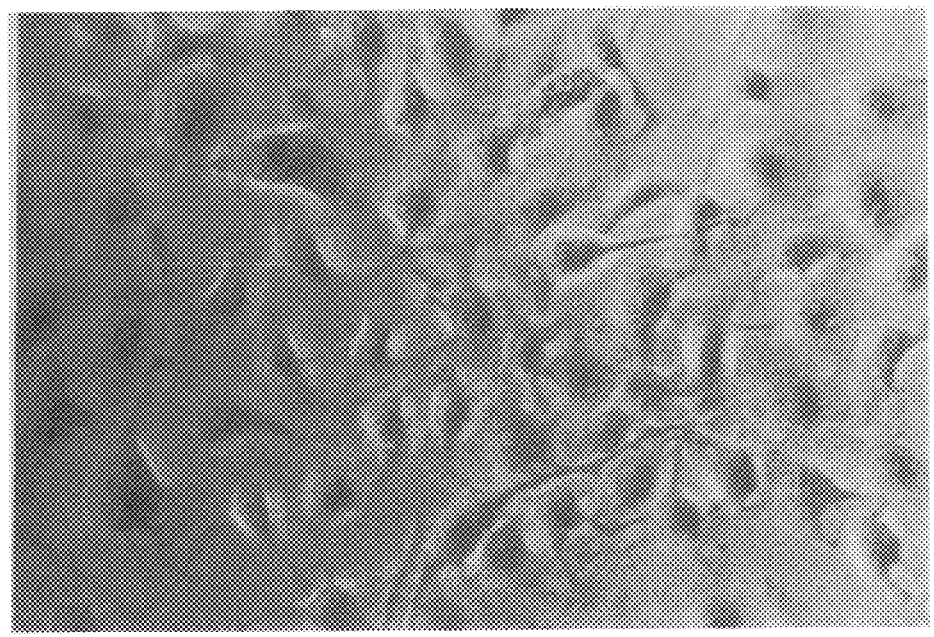
FIG. 9. The in vitro transduction of legal gene into SMMC-7721 human hepatoma cells mediated by the E5 4 element complex, stained by X gal.
Figure 10:
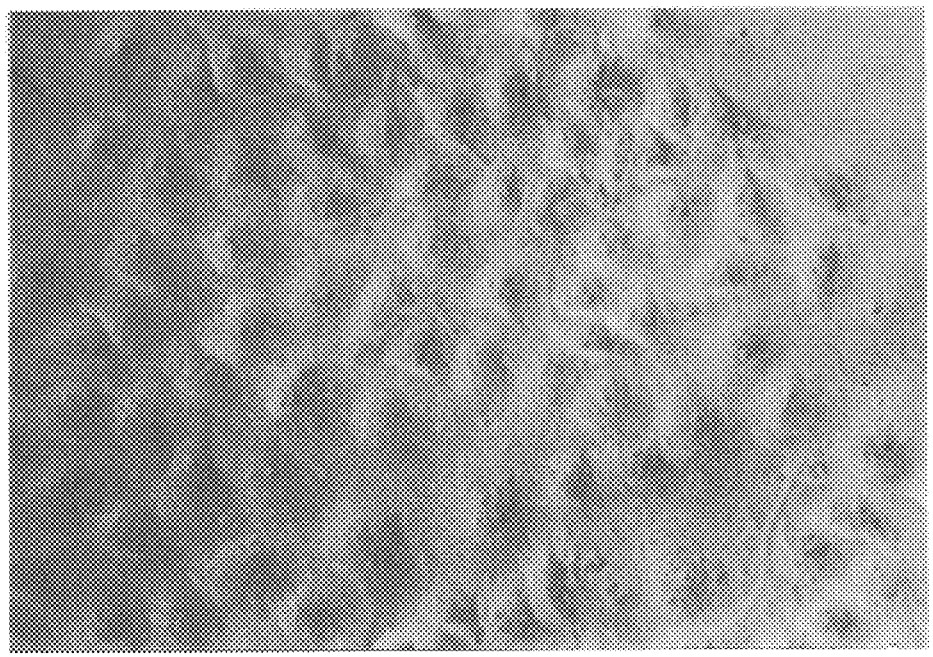
FIG. 10. The SMMC-7721 cells treated with PBS were stained with X-gal as control of FIG. 9.
Figure 11:
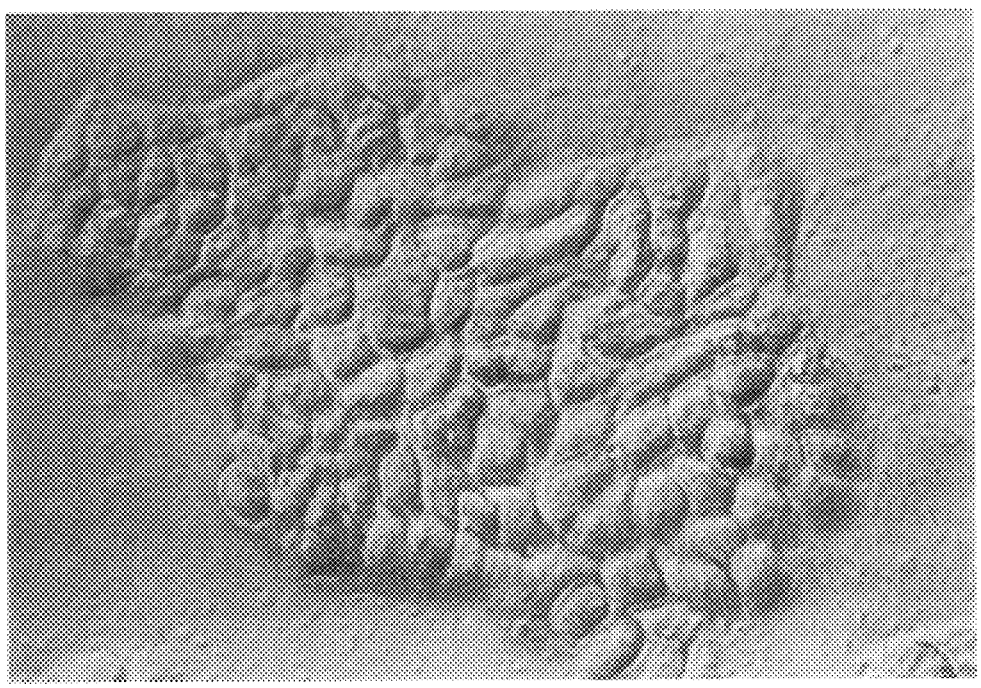
FIG. 11. The in vitro transduction of β-gal gene with E5 4 element complex into human hepatocyte cell line L02. The negative results indicate no transduction of β-gal gene by the E5 4 element complex.
Figure 12:
FIG. 12. The in vitro transduction of β-gal gene into human primary cultured hepatocytes by E5 4 element system. The negative results indicate no transduction of β-gal gene into normal hepatocytes by the E5 4 element complex.
Figure 13:
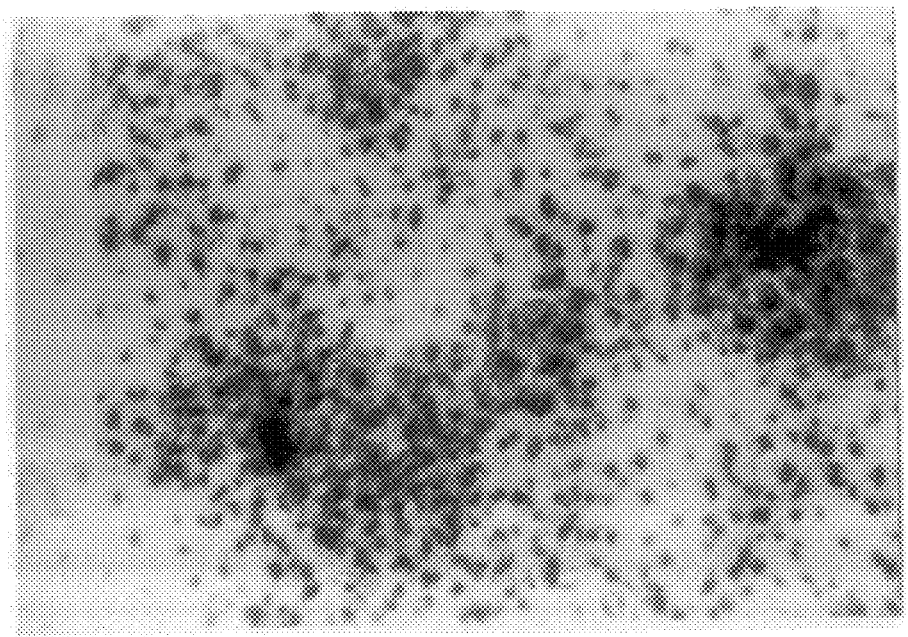
FIG. 13. The in vitro transduction of β-gal gene mediated by GE7 4 element complex into human hepatoma cell line BEL-7402. The results were shown by X-gal stain.
Figure 14:
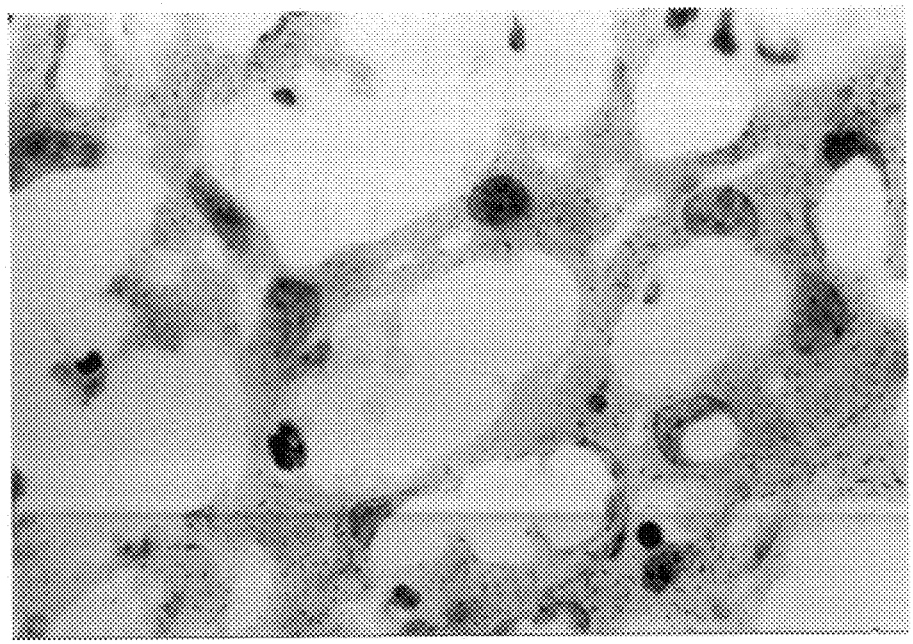
FIG. 14. The in vivo transduction of β-gal gene mediated by GV2 4 element complex into endothelial cells of capillaries in the transplanted tumor of human small cell carcinoma H128 in nude mice. Pathological section was prepared and examined after X-gal staining. The blue granules were observed in endothelial cells.
Figure 15:
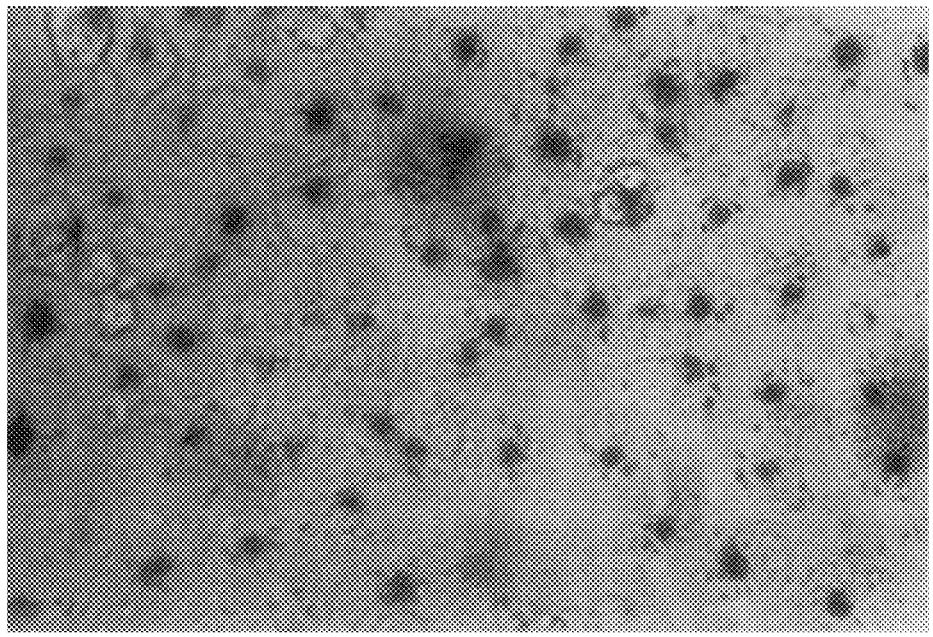
FIG. 15. The in vitro transduction of β-gal gene into human hepatoma cell line SMMC-7721 mediated by GE7 4 element complex. The positive results revealed by X-gal stain indicated the GE7 system can effectively transfer gene into hepatoma cells.
Figure 16:
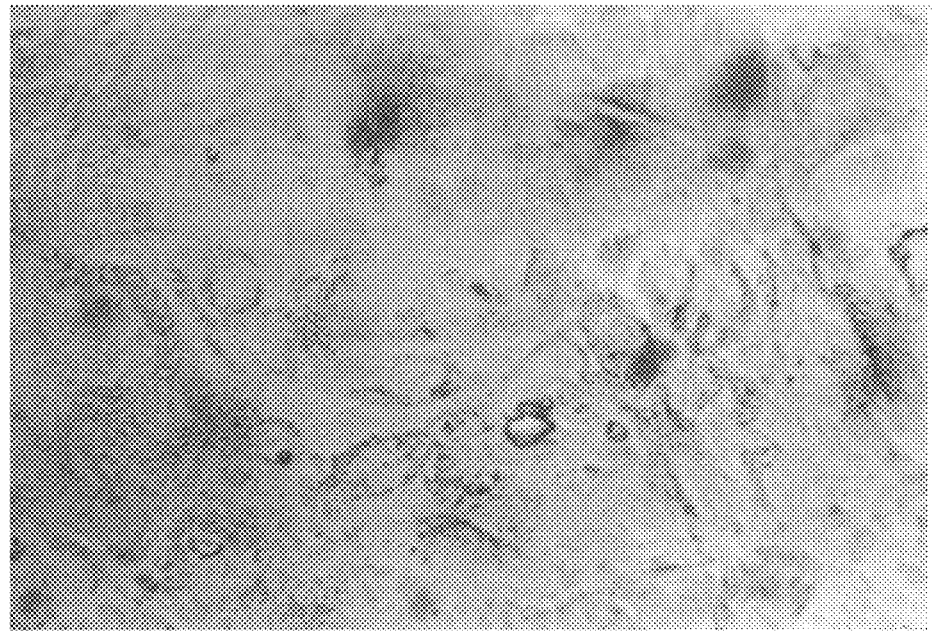
FIG. 16. The in vitro transduction of β-gal into human glioma cell line U87 cells mediated by GE7 4 element complex. Positive results were shown by X-gal stain.
Figure 17:
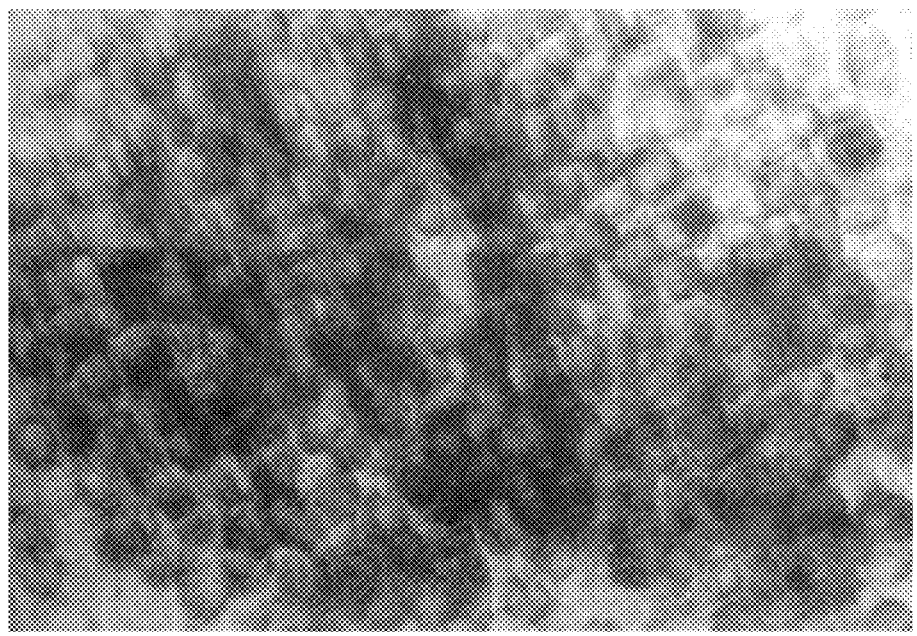
FIG. 17. The in vitro transduction of β-gal gene into human breast cancer cell line Bcap-37 cells mediated by GE7 4 element complex. Positive results were shown by X-gal stain.
Figure 18:
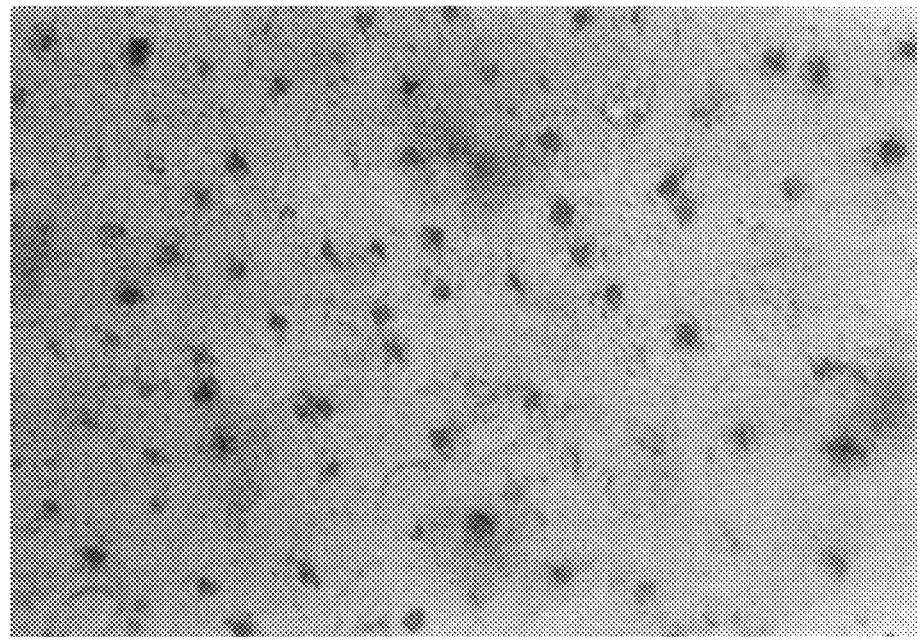
FIG. 18. The in vitro transduction of β-gal gene into human ovarian cancer cell line 3A0 cells mediated by GE7 4 element complex. Positive results were shown by X-gal stain.
Figure 19:
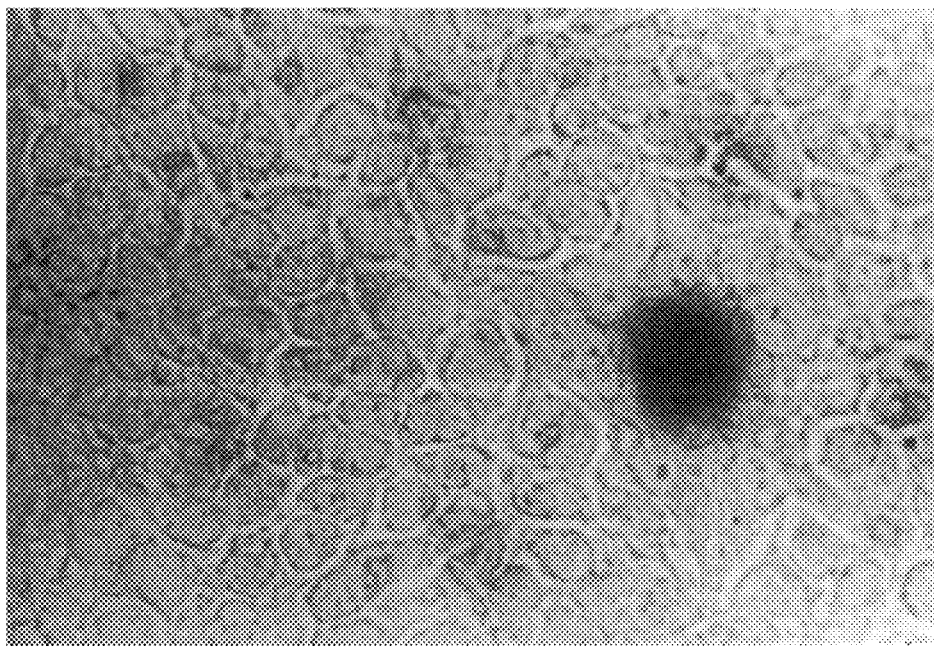
FIG. 19. The in vitro transduction of β-gal gene into human ovarian cancer cell line A0 cells mediated by GE7 4 element complex. Positive results were shown by X-gal stain.
Figure 20:
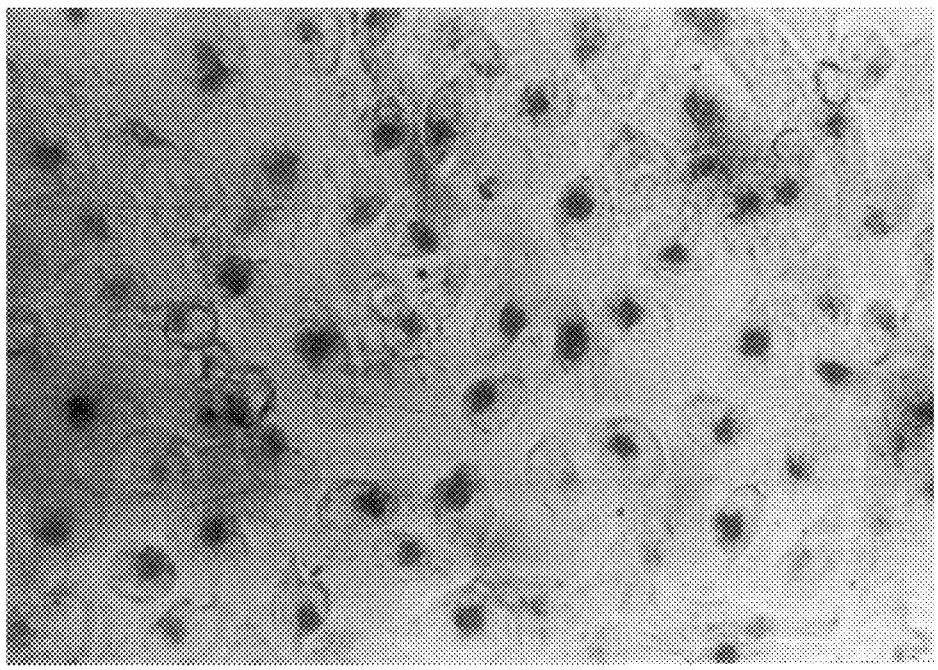
FIG. 20. The in vitro transduction of β-gal gene into human lung adenocarcinoma cell line SPC-A1 cells mediated by GE7 4 element complex. Positive results were shown by X-gal stain.
Figure 21:
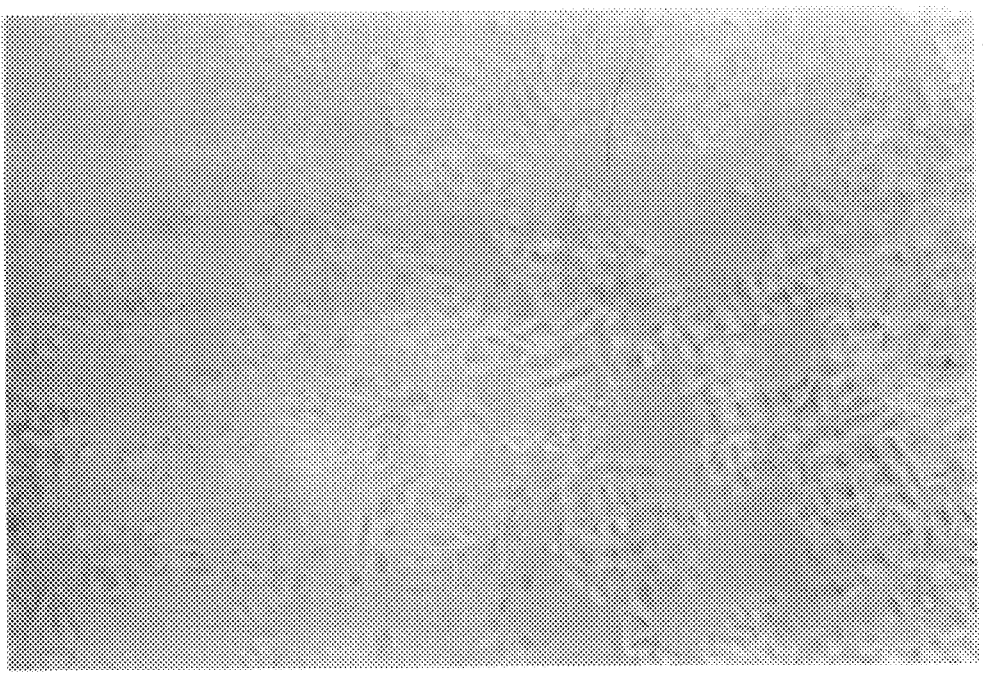
FIG. 21. The in vitro transduction of β-gal gene into normal human hepatocyte cell line L02 cells mediated by GE7 4 element complex. The negative results were shown by X-gal stain, indicating that this system can not transduce gene into normal hepatocytes.
Figure 22:
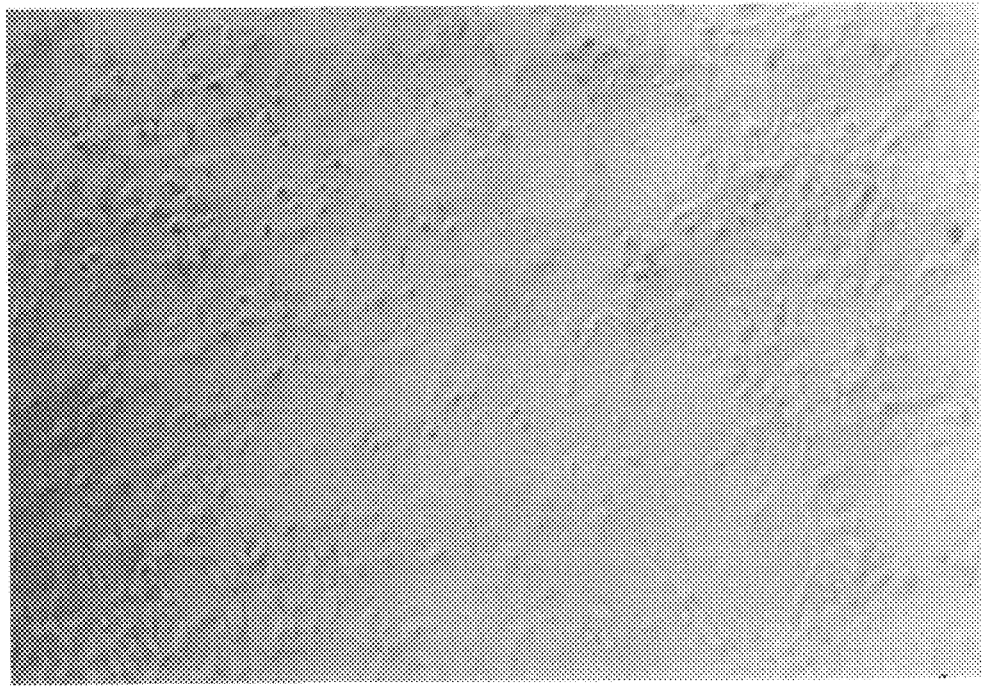
FIG. 22. The in vitro transduction of β-gal gene into NIH/3T3 cells mediated by GE7 4 element complex. The negative results revealed by X-gal stain indicated that this system can not transduce gene into mouse fibroblasts.
Figure 23:
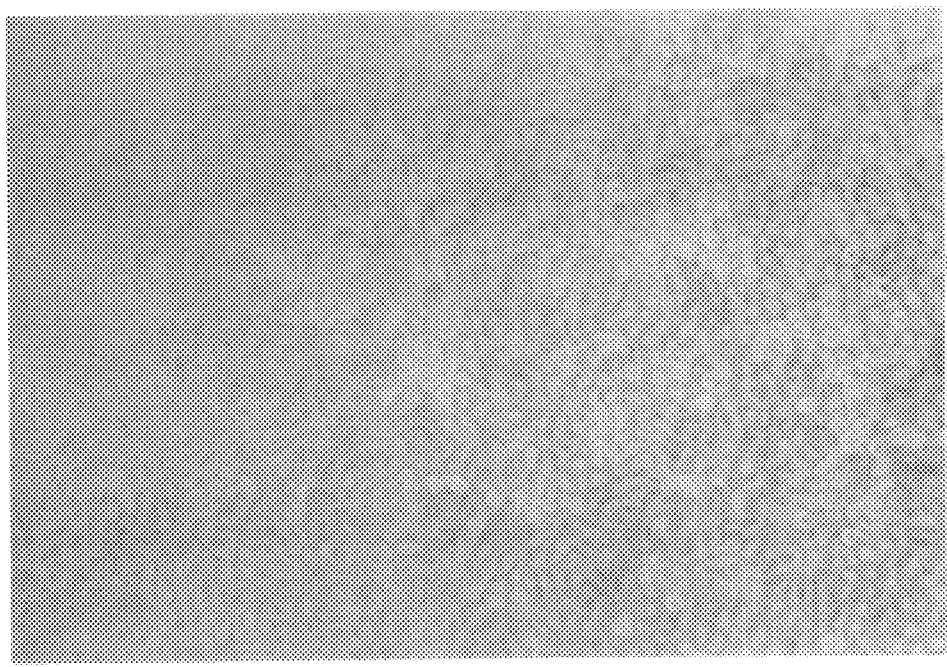
FIG. 23. The in vitro transduction of β-gal gene into human hepatoma BEL-7402 cell line mediated by HA20/polylysine/β-gal DNA complex without the GE7 or E5 oligopeptide. The negative results revealed by X-gal stain indicated that essential role of receptor specific oligopeptide for targeting cancer cells. Referred to FIG. 13 for comparison.
Figure 24:
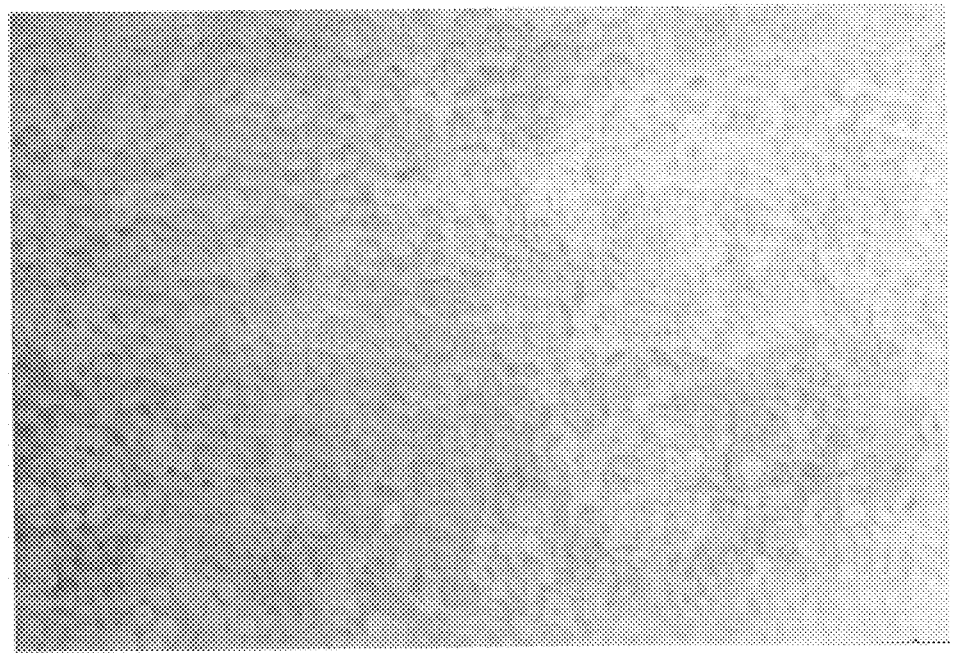
FIG. 24. The in vitro transduction of β-gal gene into human hepatoma BEL-7402 cell line mediated by polylysine/β-gal DNA complex. The negative results were observed after X-gal staining.
Figure 25:
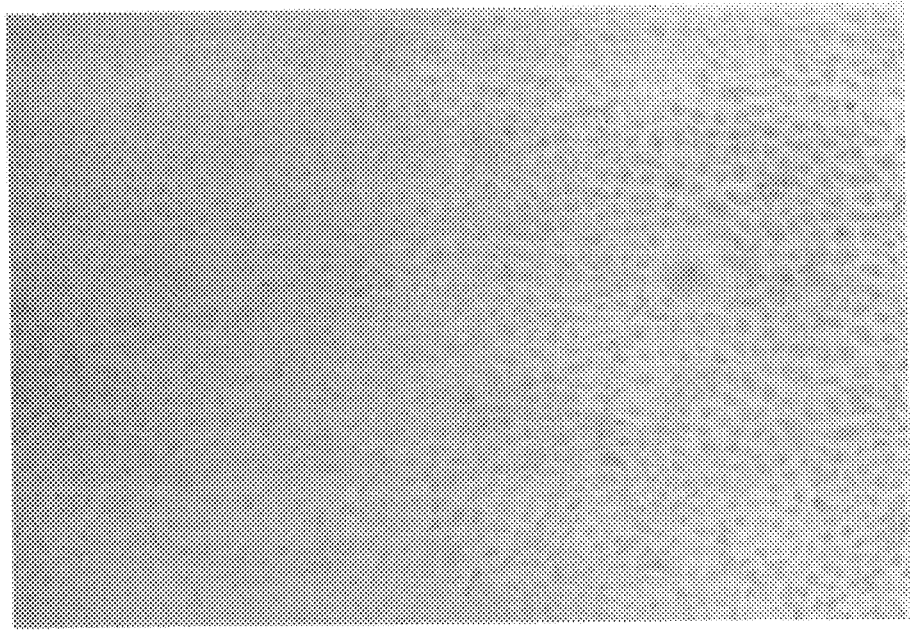
FIG. 25. Results of in vitro transduction of β-gal gene DNA alone without adding any polypeptides or transfection reagents in human hepatoma cell line BEL-7402. Negative results were observed by X-gal stain.
Figure 26:
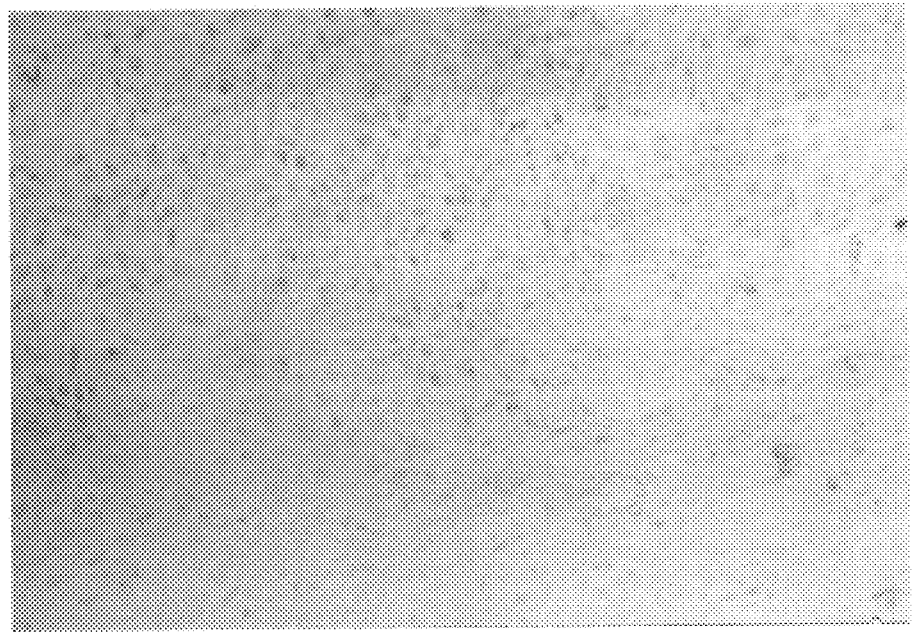
FIG. 26. Results of in vitro transduction of β-gal gene in human hepatoma cell line BEL-7402 mediated by GE7/polylysine/β-gal DNA without HA20. Positive staining by X-gal was observed only in small number of scattered cells.
Figure 27:
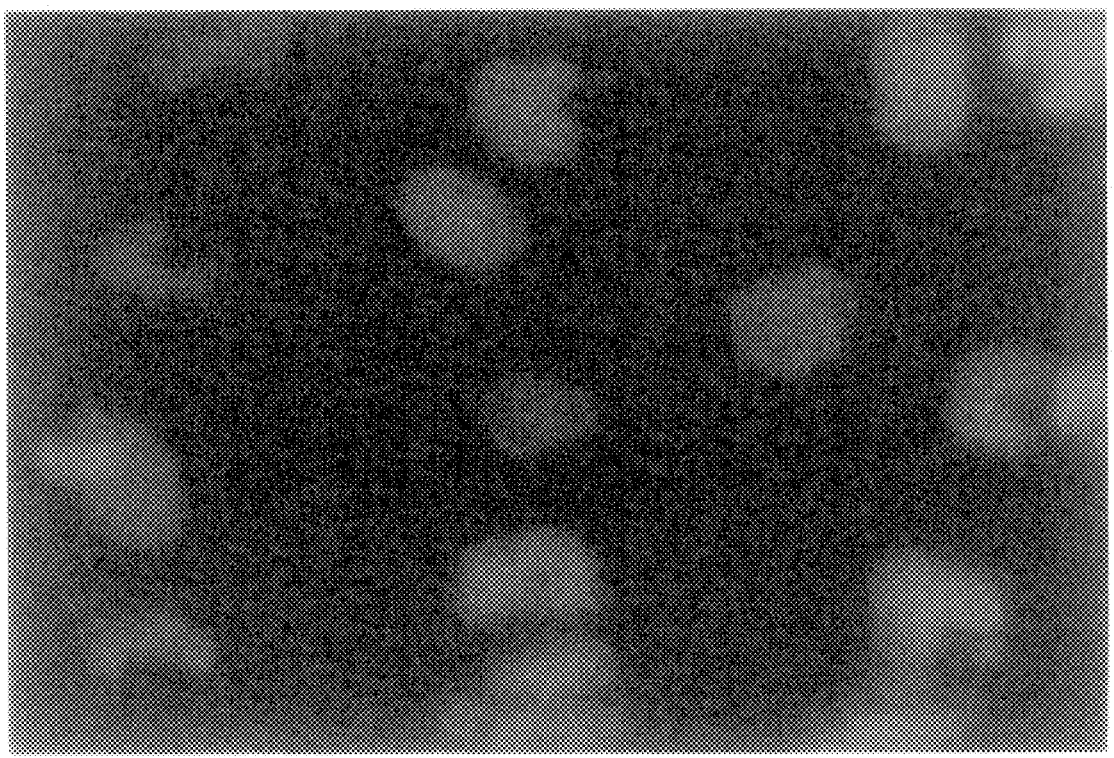
FIG. 27. Apoptosis of human hepatoma cell line SMMC-7721 cells induced by $p21^{WAF-1}$ cDNA transuded in vitro by E5 4 element complex. The apoptotic cells were shown by DAP I stain examined under fluorescence microscope.
Figure 28:
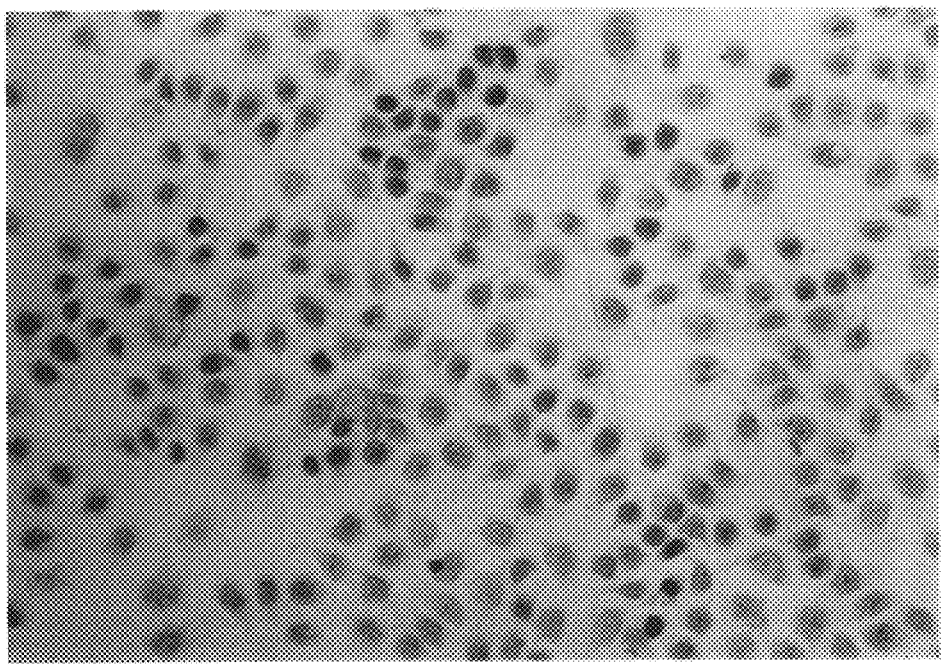
FIG. 28. Apoptosis of human hepatoma cell line SMMC-7721 cells transduced in vitro with $p21^{WAF-1}$ cDNA by E5 4 element complex. The apoptotic cells were revealed by in situ terminal nucleotide labeling techniques.
Figure 29:
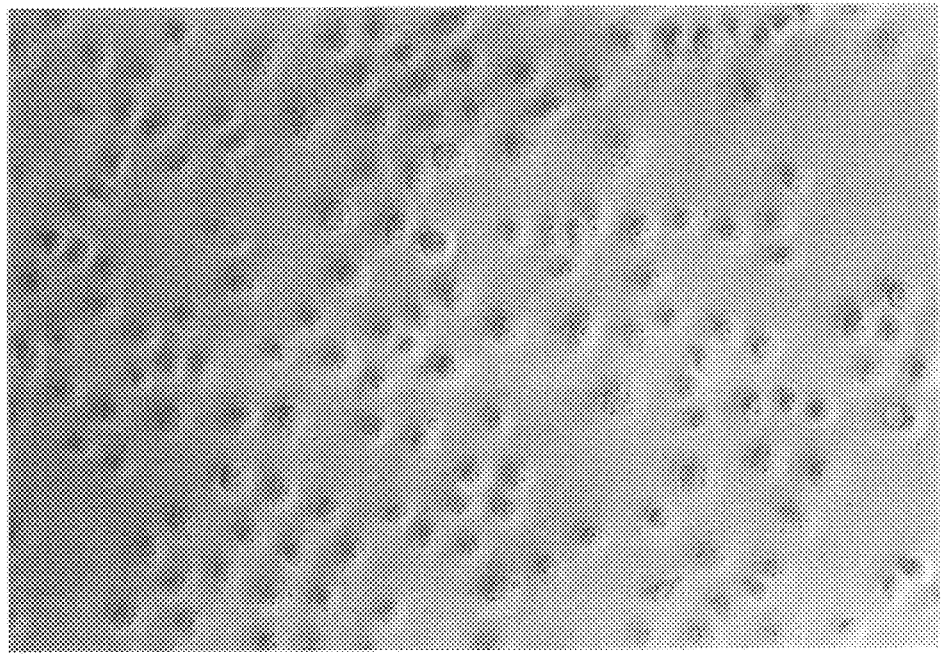
FIG. 29. Results of a control experiment for FIG. 28. The SMMC-7721 cells were transduced with E5 polypeptide vector without $p21^{WAF-1}$ cDNA.

11.3.2. Preparation of GV1-protamine/HA20-protamine/β-gal DNA and GV2-protamine/HA20-protamine/β-gal DNA 4-element complex GV1-protamine or GV2-protamine, HA20-protamine and β-gal DNA were sterilized by filtration through 0.22 μm filters. β-gal DNA was dissolved in small amount of steriled water. HA20-protamine was added dropwise and reacted at 25° C. for 5 min. GV1-protamine or GV2-protamine was then added dropwise with constant stirring. Reaction was carried out for 30 min and then diluted with normal saline. The optimal ratio of β-gal DNA to polypeptide(HA20-protamine plus GV1-protamine or GV2-protamine) was 1:5 (w/w), equivalent to a molar ratio of 1:686. The complex was monitored as Example 6 (FIG. 8).

11.4. In vivo gene transduction mediated by GV2 4-element complex to target genes into human hepatoma intrahepatically transplanted in nude mice.

Figure 43:
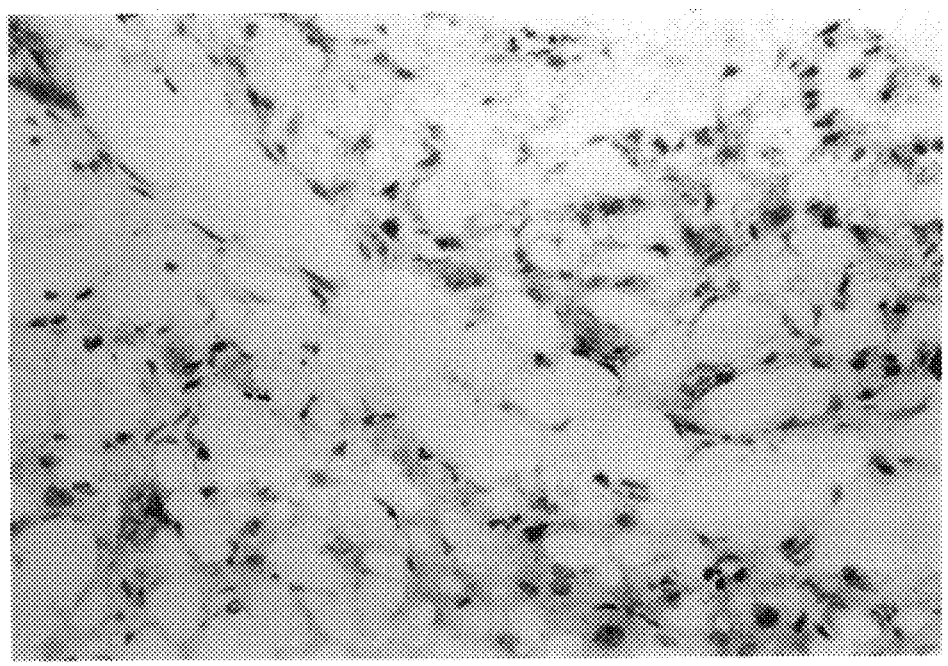
FIG. 43. The histopathological and X-gal cytochemistry examination of human lung small cell carcinoma H128 transplanted in nude mice transduced in vivo with β-gal gene mediated by GV2 4 element system. Positive staining was observed in vascular endothelial cells in tumor as well as in some of the H128 cells, indicating that GV2 system could transfer gene into tumor vascular endothelial cells.
Figure 44:
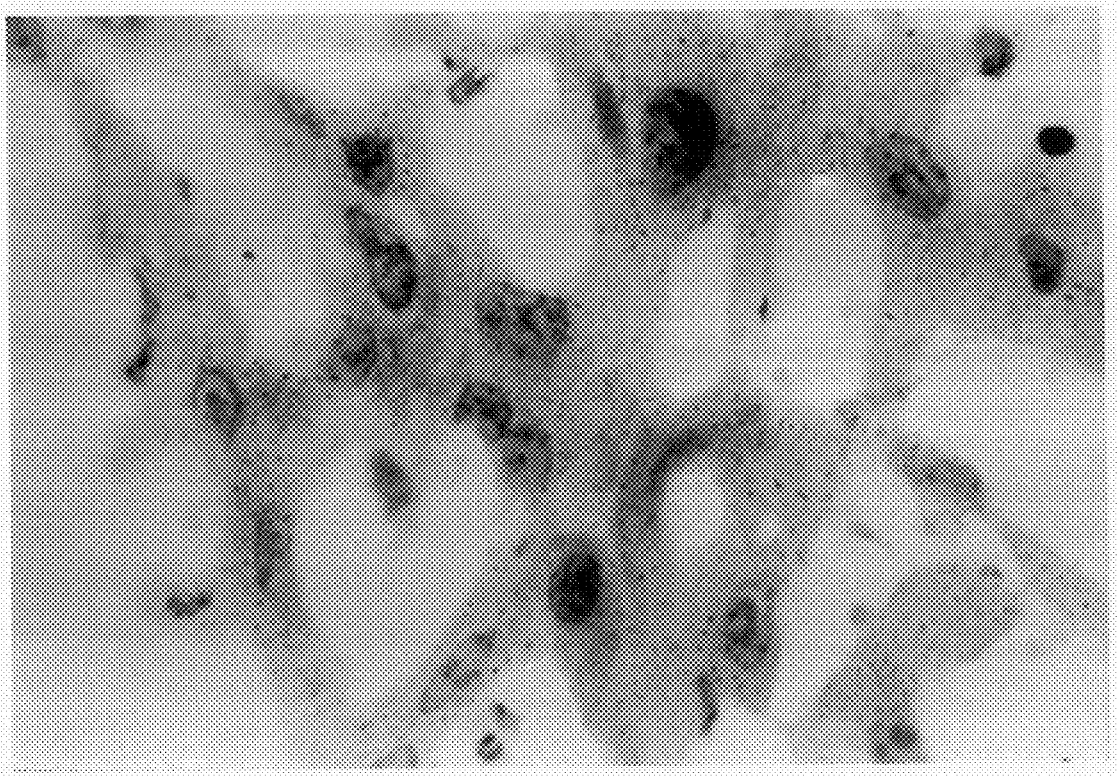
FIG. 44. The same pathological feature at high magnitude as FIG. 43. Positive staining was observed in tumor vascular endothelial cells.

50 μl GV2 4-element complex containing 0.5 kg pSV-β-gal DNA was injected into portal vein of nude mice in which human hepatic cancer was transplanted in liver. The hepatoma was a highly metastatic transplantable tumor in nude mice provided by Dr. Z. Y. Tang's laboratory, Institute of Hepatic Cancer, Zhong Shan Hospital, Shanghai Medical university. Animals were sacrificed 14 days after treatment. Tissues were collected and stained with X-gal. Frozen sections were counterstained with Hematoxylene or Fast Nuclear Red and examined under microscope. High β-gal activity was observed in endothelial cells of tumor capillaries and small blood vessels, particularly in area close to necrosis. β-gal expression was also observed in hepatoma cells in peripheral infiltration area(FIG. 43). Only low β-gal activity was observed in endothelial cells of large blood vessels. No β-gal expression was observed in liver cells.

100 μl GV2 4-element complex containing 1 μg β-gal DNA was injected into human hepatoma transplanted subcutaneously in nude mice. Animals were sacrificed 2 day after treatment. Tissues were collected and stained with X-gal. The frozen section was counterstained and examined under microscope. β-gal was expressed in endothelial cells of tumor capillaries and small blood vessels but not in liver cells.

SEQUENCE LISTING

```
<160> NUMBER OF SEQ ID NOS: 5

<210> SEQ ID NO 1
<211> LENGTH: 14
<212> TYPE: PRT
<213> ORGANISM: Artificial Sequence
<220> FEATURE:
<223> OTHER INFORMATION: Description of Artificial Sequence: Ligand
      oligopeptide  for the receptor region of IGF I and
      IGF II

<400> SEQUENCE: 1

Glu Pro Phe Arg Ser Pro Lys Leu Ala Leu Glu Thr Tyr Gly
 1               5                  10

<210> SEQ ID NO 2
<211> LENGTH: 16
<212> TYPE: PRT
<213> ORGANISM: Artificial Sequence
<220> FEATURE:
<223> OTHER INFORMATION: Description of Artificial Sequence: Ligand
      Oligopeptide  for the receptor region of EGF
      receptor.

<400> SEQUENCE: 2

Asn Pro Val Val Gly Tyr Ile Gly Glu Arg Pro Gln Tyr Arg Asp Leu
 1               5                  10                  15

<210> SEQ ID NO 3
<211> LENGTH: 32
```

```
<212> TYPE: PRT
<213> ORGANISM: Artificial Sequence
<220> FEATURE:
<223> OTHER INFORMATION: Description of Artificial Sequence: Ligand
      oligopeptide for the receptor region of VEGF.

<400> SEQUENCE: 3

Cys His Pro Ile Glu Thr Leu Val Asp Ile Phe Gln Glu Tyr Pro Asp
 1               5                  10                  15

Glu Ile Glu Tyr Ile Phe Lys Pro Ser Pro Val Pro Leu Met Arg Pro
            20                  25                  30

<210> SEQ ID NO 4
<211> LENGTH: 36
<212> TYPE: PRT
<213> ORGANISM: Artificial Sequence
<220> FEATURE:
<223> OTHER INFORMATION: Description of Artificial Sequence: Ligand
      oligopeptide for the receptor region of VEGF.

<400> SEQUENCE: 4

Pro Val Pro Thr Glu Glu Ser Asn Ile Thr Met Gln Ile Met Arg Ile
 1               5                  10                  15

Lys Pro His Gln Gly Gln His Ile Gly Glu Met Ser Phe Leu Gln His
            20                  25                  30

Asn Lys Cys Glu
            35

<210> SEQ ID NO 5
<211> LENGTH: 20
<212> TYPE: PRT
<213> ORGANISM: Artificial Sequence
<220> FEATURE:
<223> OTHER INFORMATION: Description of Artificial Sequence: Protein
      envelope of viral influenza.

<400> SEQUENCE: 5

Gly Leu Phe Glu Ala Ile Ala Glu Phe Ile Glu Gly Gly Trp Glu Glu
 1               5                  10                  15 selected from the group consisting of viral vectors and non-viral vectors.

9. The receptor-mediated composite polypeptide vector of claim 6, wherein said antisense sequence is selected from the group consisting of an antisense sequence of rasH, an antisense sequence of rasK, an antisense sequence of rasN, an antisense sequence of c-myc, an antisense sequence of bcl-2, and an antisense sequence of growth factor receptor.

10. The receptor-mediated composite polypeptide vector of claim 9, wherein said antisense sequence is in a form of plasmid DNA.

11. The receptor-mediated composite polypeptide vector of claim 9, wherein said antisense sequence is in a form of oligoribonucleotides.

12. The receptor-mediated composite polypeptide vector of claim 9, wherein said antisense sequence is in a form of oligodeoxyribonucleotides.

13. The receptor-mediated composite polypeptide vector of claim 6, wherein said cancer suppressor gene is selected from the group consisting of p53 and Rb.

14. The receptor-mediated composite polypeptide vector of claim 6, wherein said suicide gene is selected from the group consisting of Herpes Simplex Virus thymidine kinase (HSV-TK) gene and $E.$ $Coli$ cytosine deaminase (CD) gene.

15. The receptor-mediated composite polypeptide vector of claim 6, wherein said apoptosis inducing gene or cell cycle regulatory gene is selected from the group consisting of p15, p16 and p21$^{WAF-1}$.

16. The receptor-mediated composite polypeptide vector of claim 6, wherein said cytokine gene is selected from the group consisting of genes of Granulocyte-Monocyte colony stimulating factor, tumor necrosis factor $\alpha$, interferon $\alpha$, interferon $\beta$, interferon $\gamma$, interleukin 2, interleukin 3, interleukin 4, interleukin 12, and interleukin 15.

17. The receptor-mediated composite polypeptide vector of claim 1, wherein said PCP and said LOP are covalently bound to form PCP-LOP.

18. The receptor-mediated composite polypeptide vector of claim 17 wherein said PCP-LOP is covalently bound with said HA20 to form LOP-PCP-HA20 composite polypeptide vector that binds with DNA.

19. The receptor-mediated composite polypeptide vector of claim 1, wherein said HA20 is covalently bound with PCP to form HA20-PCP.

20. The receptor-mediated composite polypeptide vector of claim 19, wherein said HA20-PCP binds with an LOP-PCP complex to form a complex with DNA from the exogenous gene.

21. The receptor-mediated composite polypeptide vector of claim 1, wherein said receptor is expressed in cell lines selected from the group consisting of hemopoietic cells, macrophages, lymphocytes, hepatocytes, renal cells, vascular endothelial cells, neural and cardiac muscles.

22. The receptor-mediated composite polypeptide vector of claim 1, wherein said vector is used to transduce an exogenous gene into tumor cells in vitro, ex vivo or in vivo for cancer gene therapy.

23. The receptor-mediated composite polypeptide vector of claim 1 comprising two or more types of LOPs selected from the group consisting of E5, GE7, GV1, and GV2 for targeting IGF-I R, IGF-II R, EGF-R, and VEGF-R.

24. The receptor-mediated composite polypeptide vector of claim 1 wherein two or more types of DNA are transduced from the exogenous gene selected from the group consisting of an antisense sequence of a protooncogene, a cancer suppressor gene, a suicide gene, an apoptosis inducing gene, a cell cycle regulatory gene, and a cytokine gene.

25. The receptor-mediated composite polypeptide vector of claim 1, wherein said vector can be produced by genetic engineering techniques.

26. A receptor-mediated composite polypeptide vector for gene transfer comprising:

(i) a ligand oligopeptide (LOP) for recognition of growth factor receptor, wherein said LOP is selected from the group consisting of E5, GE7, GV1, and GV2;

(ii) a polycationic polypeptide (PCP) selected from the group consisting of polylysine, protamine, or histone; and (iii) a recombinant virus;

wherein the amino acid sequence of said E5 comprises SEQ ID NO. 1;

wherein the amino acid sequence of said GE7 comprises SEQ ID NO. 2;

wherein the amino acid sequence of said GV1 comprises SEQ ID NO. 3; and wherein the amino acid sequence of said GV2 comprises SEQ ID NO. 4.

27. The receptor-mediated composite polypeptide vector of claim 26, wherein the recombinant virus has genetically engineered adenovius or retrovirus containing exogenous genes.

28. The receptor-mediated composite polypeptide vector of claim 27, wherein the exogenous genes are selected from the group consisting of an antisense sequence of a protooncogene, a cancer suppressor gene, a suicide gene, an apoptosis-inducing gene, a cell-cycle regulatory gene, and a cytokine gene.

29. The receptor-mediated composite polypeptide vector of claim 28, wherein said antisense sequence is selected from the group consisting of an antisense sequence of rasH, an antisense sequence of rasK, an antisense sequence of rasN, an antisense sequence of c-myc, an antisense sequence of bcl-2, and an antisense sequence of growth factor receptor, either in a form of double-stranded DNA or in a form of antisense oligoribonucleotides or oligodeoxyribonucleotides.

30. The receptor-mediated composite polypeptide vector of claim 29, wherein said antisense sequence is in a form of plasmid DNA.

31. The receptor-mediated composite polypeptide vector of claim 29, wherein said antisense sequence is in a form of oligoribonucleotides.

32. The receptor-mediated composite polypeptide vector of claim 29, wherein said antisense sequence is in a form of oligodeoxyribonucleotides.

33. The receptor-mediated composite polypeptide vector of claim 28, wherein said cancer suppressor gene is selected from the group consisting of p53 and Rb.

34. The receptor-mediated composite polypeptide vector of claim 28, wherein said suicide gene is selected from the group consisting of Herpes Simplex Virus thymidine kinase (HSV-TK) gene and $E.$ $Coli$ cytosine deaminase (CD) genes.

35. The receptor-mediated composite polypeptide vector of claim 28, wherein said apoptosis inducing gene or cell cycle regulatory gene is selected from the group consisting of p15, p16 and P21$^{WAF-1}$.

36. The receptor-mediated composite polypeptide vector of claim 28, wherein said cytokine gene is selected from the group consisting of genes of Granulocyte-Monocyte colony stimulating factor, tumor necrosis factor $\alpha$, interferon $\alpha$, interferon $\beta$, interferon $\gamma$, interleukin 2, interleukin 3, interleukin 4, interleukin 12, and interleukin 15.

37. The receptor-mediated composite polypeptide vector of claim 26, wherein the recombinant virus does not contain exogenous genes.

38. The receptor-mediated composite polypeptide vector of claim of 26, wherein said E5 can bind to growth factor receptor IGF-I R.

39. The receptor-mediated composite polypeptide vector of claim 26, wherein said E5 can bind to growth factor receptor IGF-II R.

40. The receptor-mediated composite polypeptide vector of claim 26, wherein said GE7 can bind to growth factor receptor EGF R.

41. The receptor-mediated composite polypeptide vector of claim 26, wherein said GV1 and GV2 can bind to growth factor receptor VEGF R.

42. The receptor-mediated composite polypeptide vector of claim 28, wherein said gene or sequences are cloned into eukaryotic expression vectors, wherein said vectors are driven by cis regulatory elements of SV40 or CMV.

43. The receptor-mediated composite polypeptide vector of claim 42, wherein said eukaryotic expression vectors are selected from the group consisting of viral vectors and non-viral vectors.

* * * * *